(12) United States Patent
Donohoe et al.

(10) Patent No.: US 11,666,105 B2
(45) Date of Patent: Jun. 6, 2023

(54) WEARABLE ARTICLE WITH REMOVABLE MODULE

(71) Applicant: NIKE, Inc., Beaverton, OR (US)

(72) Inventors: Brendan Donohoe, Portland, OR (US); Keith Folske, Wilsonville, OR (US); Brian L. Kash, Portland, OR (US); Kevin Steward, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 15/951,743

(22) Filed: Apr. 12, 2018

(65) Prior Publication Data

US 2018/0295896 A1 Oct. 18, 2018

Related U.S. Application Data

(60) Provisional application No. 62/484,732, filed on Apr. 12, 2017, provisional application No. 62/484,739, filed on Apr. 12, 2017.

(51) Int. Cl.
*G08B 23/00* (2006.01)
*A41D 1/00* (2018.01)
(Continued)

(52) U.S. Cl.
CPC .......... *A41D 1/002* (2013.01); *A61B 5/02055* (2013.01); *A61B 5/681* (2013.01);
(Continued)

(58) Field of Classification Search
CPC .. A41D 1/002; A61B 5/02055; A61B 5/6807; A61B 5/681; A61B 5/11; A61B 5/6805;
(Continued)

(56) References Cited

U.S. PATENT DOCUMENTS 1,531,994 A * 3/1925 Starmer ................. A41F 9/002
2/171
3,160,910 A * 12/1964 Quinn ....................... E05F 3/02
188/298
(Continued)

FOREIGN PATENT DOCUMENTS

AU 2002100391 A4 6/2002
CN 2708689 Y 7/2005
(Continued)

OTHER PUBLICATIONS

USB-Chargeable Emergency Inspection Light, May 2016.*
(Continued)

*Primary Examiner* — Quang Pham
(74) *Attorney, Agent, or Firm* — Banner & Witcoff, Ltd.

(57) ABSTRACT

A system includes an electronic module containing an electronic component and a connector in communication with the electronic component, and a housing defining a chamber and having an opening providing access to the chamber to receive the electronic module. The housing has an interface for removable electronic connection to the connector of the module when the module is received in the chamber, and the housing further has a magnet connected to the housing. The module includes a sensor configured to sense the magnet when the module is received in the chamber, and the module is configured to deactivate the connector when the sensor does not sense the magnet and to activate the connector when the sensor does sense the magnet. The sensor may be a Hall effect sensor and/or the connector may be configured for connection to a USB port in various configurations.

4 Claims, 21 Drawing Sheets

(51) Int. Cl.
*A61B 5/00* (2006.01)
*A61B 5/0205* (2006.01)
*G06F 1/16* (2006.01)
*G06F 3/01* (2006.01)
*A61B 5/11* (2006.01)

(52) U.S. Cl.
CPC ............ *A61B 5/6807* (2013.01); *G06F 1/163* (2013.01); *A61B 5/11* (2013.01); *A61B 5/6805* (2013.01); *A61B 5/6806* (2013.01); *A61B 2562/0204* (2013.01); *A61B 2562/0219* (2013.01); *A61B 2562/0247* (2013.01); *G06F 3/011* (2013.01)

(58) Field of Classification Search
CPC .......... A61B 5/6806; A61B 2562/0204; A61B 2562/0219; A61B 2562/0247; G06F 1/163; G06F 3/011
See application file for complete search history.

(56) References Cited

U.S. PATENT DOCUMENTS

| | | | |
|---|---|---|---|
| 4,313,445 A | 2/1982 | Georgi | |
| 4,462,116 A * | 7/1984 | Sanzone | A41D 20/00 2/253 |
| 4,709,307 A * | 11/1987 | Branom | A41D 27/085 362/108 |
| 4,832,010 A * | 5/1989 | Lerman | A61F 13/061 2/24 |
| 5,155,442 A * | 10/1992 | Mercer | G01V 3/15 324/686 |
| 5,353,793 A * | 10/1994 | Bornn | A61B 5/282 607/152 |
| 5,547,115 A * | 8/1996 | Ambrosius | A45F 5/02 224/904 |
| 5,613,756 A * | 3/1997 | Allen | A41D 27/085 362/189 |
| 5,809,576 A * | 9/1998 | Huston | A41D 27/20 2/248 |
| 6,178,343 B1 * | 1/2001 | Bindszus | A61B 5/14551 600/323 |
| 6,425,137 B1 * | 7/2002 | Fakhrai | A45C 1/04 2/338 |
| 6,563,424 B1 * | 5/2003 | Kaario | G06F 1/163 340/572.1 |
| 7,736,310 B2 | 6/2010 | Taub | |
| 8,105,208 B2 * | 1/2012 | Oleson | A44B 18/00 482/901 |
| 8,375,471 B2 * | 2/2013 | Surve | D06M 10/06 2/243.1 |
| 8,381,989 B2 * | 2/2013 | O'Neill | A44C 5/14 235/487 |
| 9,141,087 B2 | 9/2015 | Brown et al. | |
| 9,521,868 B2 | 12/2016 | Cobbett et al. | |
| 9,734,477 B2 * | 8/2017 | Weast | G04G 21/025 |
| 2002/0044052 A1 * | 4/2002 | Stewart | B62J 6/056 340/475 |
| 2002/0124295 A1 * | 9/2002 | Fenwick | A41D 13/1245 2/69 |
| 2002/0163800 A1 * | 11/2002 | Hansen | A44B 1/04 362/234 |
| 2004/0010199 A1 * | 1/2004 | Hashimoto | A61B 5/02444 600/502 |
| 2004/0081025 A1 * | 4/2004 | Chen | G04G 21/00 368/10 |
| 2004/0171464 A1 * | 9/2004 | Ashby | A63B 22/00 482/8 |
| 2004/0250933 A1 * | 12/2004 | DeMichele | A45C 1/08 150/145 |
| 2005/0119833 A1 * | 6/2005 | Nanikashvili | G16H 40/67 702/19 |
| 2006/0026730 A1 * | 2/2006 | Terczak | A41D 13/08 2/59 |
| 2006/0075537 A1 * | 4/2006 | Tsai | A41D 27/205 2/69 |
| 2006/0117458 A1 * | 6/2006 | Ishihara | A41D 1/002 2/170 |
| 2007/0011919 A1 * | 1/2007 | Case | A43B 1/0036 36/132 |
| 2007/0021269 A1 * | 1/2007 | Shum | A61B 5/6831 482/8 |
| 2007/0026695 A1 | 2/2007 | Lee et al. | |
| 2007/0106133 A1 * | 5/2007 | Satchwell | A61B 5/14532 600/509 |
| 2007/0194066 A1 * | 8/2007 | Ishihara | A41D 1/002 224/164 |
| 2007/0260421 A1 * | 11/2007 | Berner, Jr. | G01C 22/006 702/155 |
| 2007/0261703 A1 | 11/2007 | Gheneva et al. | |
| 2007/0279852 A1 | 12/2007 | Daniel et al. | |
| 2007/0300174 A1 | 12/2007 | Macbeth et al. | |
| 2008/0045872 A1 * | 2/2008 | Bauerfeind | A61F 13/148 607/2 |
| 2008/0058668 A1 * | 3/2008 | Seyed Momen | A61F 2/72 600/546 |
| 2008/0125288 A1 * | 5/2008 | Case | A43B 3/34 600/300 |
| 2008/0141436 A1 * | 6/2008 | Morgan | B63C 11/02 2/170 |
| 2008/0301853 A1 | 12/2008 | Cummiskey et al. | |
| 2009/0012542 A1 * | 1/2009 | N'diaye | A61F 5/0079 606/153 |
| 2009/0105795 A1 * | 4/2009 | Minogue | A61N 1/321 607/148 |
| 2009/0113089 A1 * | 4/2009 | Liu | G06F 1/266 710/63 |
| 2009/0292118 A1 * | 11/2009 | Lee | C07D 498/18 540/456 |
| 2009/0292178 A1 | 11/2009 | Ellis et al. | |
| 2010/0010357 A1 * | 1/2010 | Ostrowiecki | A61B 5/02233 600/499 |
| 2010/0032462 A1 * | 2/2010 | Cameron | A45F 5/00 224/267 |
| 2010/0063652 A1 * | 3/2010 | Anderson | G08C 17/02 235/494 |
| 2010/0268056 A1 * | 10/2010 | Picard | A61B 5/6804 600/300 |
| 2011/0025195 A1 * | 2/2011 | Govender | F21V 33/0008 313/504 |
| 2011/0057003 A1 * | 3/2011 | Wysocki | A45C 11/00 224/222 |
| 2011/0199779 A1 * | 8/2011 | Chu | F21V 33/0008 362/103 |
| 2011/0205161 A1 * | 8/2011 | Myers | A63F 13/285 345/169 |
| 2011/0235311 A1 * | 9/2011 | Stone | A42B 3/044 362/106 |
| 2011/0241627 A1 * | 10/2011 | Arai | G06F 1/26 320/162 |
| 2012/0029299 A1 * | 2/2012 | DeRemer | A61B 5/0002 600/300 |
| 2012/0035426 A1 * | 2/2012 | Mielcarz | A61B 5/0015 600/300 |
| 2012/0080462 A1 * | 4/2012 | Hajarian | A45F 5/00 224/219 |
| 2012/0099298 A1 * | 4/2012 | Hsu | A41D 27/085 362/103 |
| 2012/0136231 A1 * | 5/2012 | Markel | A42B 1/006 600/388 |
| 2012/0174278 A1 * | 7/2012 | Spivak | A41D 13/08 2/16 |
| 2012/0229248 A1 * | 9/2012 | Parshionikar | G08B 21/06 340/3.1 |
| 2012/0246795 A1 * | 10/2012 | Scheffler | A63B 24/0062 2/243.1 |
| 2012/0296174 A1 * | 11/2012 | McCombie | A61B 5/332 600/595 |
| 2013/0131484 A1 * | 5/2013 | Pernu | A61B 5/0245 600/388 |

(56) References Cited

U.S. PATENT DOCUMENTS

| | | | |
|---|---|---|---|
| 2013/0237882 A1* | 9/2013 | Niemimaki | A61B 5/11 600/595 |
| 2013/0267854 A1* | 10/2013 | Johnson | A61B 5/721 600/479 |
| 2013/0313914 A1* | 11/2013 | Hou | G06F 1/266 307/115 |
| 2014/0012161 A1* | 1/2014 | Ross, Jr. | A41D 1/002 600/595 |
| 2014/0101493 A1* | 4/2014 | Olney | G06F 11/0754 714/47.2 |
| 2014/0107493 A1 | 4/2014 | Yuen et al. | |
| 2014/0116944 A1* | 5/2014 | Hu | B01D 69/02 96/12 |
| 2014/0131402 A1* | 5/2014 | Holmes | A45F 5/00 224/222 |
| 2014/0176944 A1 | 6/2014 | Addison et al. | |
| 2014/0189928 A1 | 7/2014 | Oleson et al. | |
| 2014/0212706 A1* | 7/2014 | Ro | H01M 2/30 429/10 |
| 2014/0213863 A1* | 7/2014 | Loseu | A61B 5/725 600/324 |
| 2014/0213917 A1* | 7/2014 | Hobeika | A61B 5/02438 600/500 |
| 2014/0243618 A1 | 8/2014 | Charles, Jr. et al. | |
| 2014/0260677 A1 | 9/2014 | Dojan et al. | |
| 2014/0268685 A1* | 9/2014 | McLisky | F21V 33/0008 362/108 |
| 2014/0276236 A1* | 9/2014 | Swain | A61B 5/1038 600/592 |
| 2014/0316305 A1* | 10/2014 | Venkatraman | A61B 5/02438 600/595 |
| 2014/0358473 A1* | 12/2014 | Goel | A61B 5/1118 702/141 |
| 2015/0011099 A1* | 1/2015 | Kim | H01R 13/502 439/38 |
| 2015/0031964 A1* | 1/2015 | Bly | A61B 5/681 600/300 |
| 2015/0148619 A1* | 5/2015 | Berg | A61B 5/6804 600/300 |
| 2015/0164349 A1* | 6/2015 | Gopalakrishnan | G16H 40/67 600/508 |
| 2015/0169074 A1* | 6/2015 | Ataee | G06F 3/017 345/156 |
| 2015/0182160 A1* | 7/2015 | Kim | A61B 5/7475 600/301 |
| 2015/0190072 A1* | 7/2015 | Armstrong | A61B 5/1118 600/300 |
| 2015/0257708 A1 | 9/2015 | Winokur et al. | |
| 2015/0267911 A1* | 9/2015 | Cushnie | G02B 6/0008 362/108 |
| 2015/0302158 A1* | 10/2015 | Morris | G06K 9/629 702/19 |
| 2015/0310333 A1* | 10/2015 | Doshi | G06F 9/46 706/46 |
| 2015/0370333 A1 | 12/2015 | Ataee et al. | |
| 2016/0007919 A1 | 1/2016 | Pemu et al. | |
| 2016/0021945 A1* | 1/2016 | Richmond | H01M 10/44 219/211 |
| 2016/0058375 A1 | 3/2016 | Rothkopf | |
| 2016/0102808 A1* | 4/2016 | Bray | F16M 13/022 248/206.2 |
| 2016/0135516 A1* | 5/2016 | Cobbett | A41D 1/002 434/247 |
| 2016/0135522 A1* | 5/2016 | Rothschild | A41D 20/00 2/170 |
| 2016/0135743 A1* | 5/2016 | Cobbett | G01C 21/3697 2/243.1 |
| 2016/0136882 A1* | 5/2016 | Cobbett | A61B 5/02438 156/218 |
| 2016/0150958 A1* | 6/2016 | Kranz | A61B 5/0006 600/515 |
| 2016/0187391 A1* | 6/2016 | Ye | H01R 13/7175 324/96 |
| 2016/0192516 A1* | 6/2016 | Thompson | A45F 5/00 224/219 |
| 2016/0192716 A1 | 7/2016 | Lee | |
| 2016/0206083 A1* | 7/2016 | Gomez | A45F 5/00 |
| 2016/0209016 A1* | 7/2016 | Bernstein | F21V 23/0492 |
| 2016/0226286 A1* | 8/2016 | Xiang | H02J 7/342 |
| 2016/0249698 A1* | 9/2016 | Berzowska | A41D 13/1281 2/69 |
| 2016/0338441 A1* | 11/2016 | London | A43B 5/00 |
| 2016/0349790 A1* | 12/2016 | Connor | G06F 3/017 |
| 2016/0374608 A1* | 12/2016 | Dugan | A61B 5/746 600/301 |
| 2017/0095692 A1* | 4/2017 | Chang | A61B 5/1118 |
| 2017/0100300 A1* | 4/2017 | Rapp | A61B 5/6828 |
| 2017/0126053 A1* | 5/2017 | Lai | H02J 9/061 |
| 2017/0172504 A1* | 6/2017 | Lee | H04B 1/385 |
| 2017/0196514 A1 | 7/2017 | Moltani et al. | |
| 2017/0332442 A1* | 11/2017 | Strecker | H05B 1/0272 |
| 2018/0003579 A1* | 1/2018 | Esposito | D04B 1/26 |
| 2018/0042550 A1* | 2/2018 | Zhang | H04B 5/00 |
| 2018/0184727 A1* | 7/2018 | Petruschka | A41D 1/002 |
| 2018/0242658 A1* | 8/2018 | Dal Lago | B62J 6/165 |
| 2018/0295895 A1* | 10/2018 | Donohoe | A61B 5/6807 |
| 2018/0295896 A1* | 10/2018 | Donohoe | A61B 5/02055 |
| 2018/0295897 A1* | 10/2018 | Donohoe | A61B 5/681 |
| 2019/0159727 A1* | 5/2019 | Macagno | A61B 5/1123 |
| 2020/0315267 A1* | 10/2020 | Donohoe | G06F 1/163 |
| 2022/0240599 A1* | 8/2022 | Donohoe | A41D 1/002 |

FOREIGN PATENT DOCUMENTS

| | | |
|---|---|---|
| CN | 2774203 Y | 4/2006 |
| CN | 101800499 A | 8/2010 |
| CN | 105722419 A | 6/2016 |
| CN | 205285056 U | 6/2016 |
| EP | 1559335 A2 | 8/2005 |
| EP | 2260910 A1 | 12/2010 |
| JP | H03015439 A | 1/1991 |
| JP | H09322882 A | 12/1997 |
| JP | H11081017 A | 3/1999 |
| JP | 2001112725 A | 4/2001 |
| JP | 2002216282 A | 8/2002 |
| JP | 2002222263 A | 8/2002 |
| JP | 2006312010 A | 11/2006 |
| JP | 2007521030 A | 8/2007 |
| JP | 2008520841 A | 6/2008 |
| JP | 2008541311 A | 11/2008 |
| JP | 2009536694 A | 10/2009 |
| JP | 2009280951 A | 12/2009 |
| JP | 2010059567 A | 3/2010 |
| JP | 2010517657 A | 5/2010 |
| JP | 2011136182 A | 7/2011 |
| JP | 2011526518 A | 10/2011 |
| JP | 2011527588 A | 11/2011 |
| JP | 2012065707 A | 4/2012 |
| JP | 2012071054 A | 4/2012 |
| JP | 2013512353 A | 4/2013 |
| JP | 2013192877 A | 9/2013 |
| JP | 2014076113 A | 5/2014 |
| JP | 2014179087 A | 9/2014 |
| JP | 2014180328 A | 9/2014 |
| JP | 2015511840 A | 4/2015 |
| JP | 2016034579 A | 3/2016 |
| KR | 2014-0024845 A | 3/2014 |
| WO | 2001015286 A1 | 3/2001 |
| WO | 2006055125 A1 | 5/2006 |
| WO | 2010015030 A1 | 2/2010 |
| WO | 2010073691 A1 | 7/2010 |
| WO | 2012024139 A1 | 2/2012 |
| WO | 2012112931 A2 | 8/2012 |
| WO | 2013144866 A1 | 10/2013 |
| WO | 2014037874 A1 | 3/2014 |

(56) References Cited

FOREIGN PATENT DOCUMENTS

| | | |
|---|---|---|
| WO | 2016081752 A1 | 5/2016 |
| WO | 2016122399 A1 | 8/2016 |

OTHER PUBLICATIONS

Sayem et al., Review on Smart Electro-Clothing Systems (SeCSs) (Year: 2020).*
Feb. 18, 2016—(WO) International Search Report/Written Opinion—App PCT/US15/61691.
Feb. 18, 2016—(WO) International Search Report/Written Opinion—App PCT/US15/61675.
Feb. 24, 2016—(WO) International Search Report/Written Opinion—App PCT/US15/61676.
Shekharappa et al, Correlation between body mass index and cardiovascular parameters in obese and non-obese in different age groups, 2011, Internatinal Journal of Biological & Medical Research, 2(2): 551-555.
Weight Loss Resources, BMI Calculator, 2004, Web, Retreived from: http://www.weightlossresources.co.uk/body_weight/healthy_weight/bmi_calculator.htm.
CNET, First look: Withings Pulse a sleek wireless pedometer and heart rate monitor, 2013, Web Video. Retrieved from: https://www.youtube.com/watch?v=j8L6ls0fYmM.
Ratas, Review of Withings Pulse, 2013, Web, Retrieved from: http://technogog.com/review/reviewofwithingspulse/.
Cambridge University Engineering Department, Materials Data Book, 2003, Web, Rerieved from: http://www.mdpeng.cam.ac.uk/web/library/enginfo/dueddatabooks/materials.pdf.
May 4, 2016—(WO) ISR & WO—App PCT/US15/61694.
Funada S et al: "Body mass index and cardiovascular disease mortality in Japan: The Ohsaki Study", Preventive Medicine, Academic Press, XX, vol. 47, No. 1, Jul. 1, 2009 (Jul. 1, 2008), pp. 66-70.
Apr. 29, 2016—(WO) ISR & WO—App No. PCT/US2015/061644.
Jun. 7, 2016—(WO) ISR & WO—App No. PCT/US2015/061670.
Shad, Lessons Learnt From Breaking Things: Wrist Activity Trackers, 2013 Web, Retrieved from: http://www.mindtribe.com/2013/10/lessonslearntfrombreakinthings1/.
UM Libraries, The Michigan Technic, 1944, vols. 63-64, p. 34.
Jul. 23, 2018—(WO) ISR & WO—App No. PCT/US18/027256.
Sep. 10, 2018—(WO) ISR & WO—App. No. PCT/US18/027261.

* cited by examiner

WEARABLE ARTICLE WITH REMOVABLE MODULE

CROSS-REFERENCE TO RELATED APPLICATIONS

This application claims priority to and is a non-provisional of U.S. Provisional Application No. 62/484,732, filed Apr. 12, 2017, and also claims priority to U.S. Provisional Application No. 62/484,739, filed Apr. 12, 2017, which prior applications are incorporated herein in their entireties.

TECHNICAL FIELD

The invention relates generally to articles of apparel and other wearable articles, and more specifically, to wearable articles that have a housing mounted thereon for engagement with an electronic module.

BACKGROUND

Existing technologies provide various configurations for integration of electronic components with articles of apparel and other wearable articles. However, the structures and manufacturing methods provided by existing technologies suffer from certain limitations and drawbacks. For example, there is a need for a structure that provides the ability to mount a removable electronic module to a wearable article, and in particular a module that provides electrical power to an electrically-powered component of the article. There is also a need for an efficient and effective manufacturing method for connecting a housing for a removable electronic module to a wearable article. The devices and methods of the present disclosure are provided to address at least some of the problems discussed above and other problems, and to provide advantages and aspects not provided by prior ball striking devices of this type. A full discussion of the features and advantages of the present disclosure is deferred to the following detailed description, which proceeds with reference to the accompanying drawings.

BRIEF SUMMARY

Aspects of the present disclosure relate to a system that includes an electronic module having a casing containing at least one electronic component and a connector in communication with the at least one electronic component, and a housing defining a chamber and having an opening providing access to the chamber such that the electronic module is configured to be removably inserted into the chamber through the opening. The housing has an interface configured for removable electronic connection to the connector of the electronic module when the electronic module is received in the chamber, and the housing further has a magnet connected to the housing. The electronic module includes a sensor configured to sense the magnet when the electronic module is received in the chamber, and the electronic module is configured to deactivate the connector when the sensor does not sense the magnet and to activate the connector when the sensor does sense the magnet. The sensor may be a Hall effect sensor and/or the connector may be configured for connection to a USB port in various configurations.

According to one aspect, the interface includes a plurality of electrical contacts exposed within the chamber, and the connector includes a plurality of terminals configured to engage the electrical contacts.

According to another aspect, the electronic module includes a power supply configured to supply power to the connector, and the connector includes a power terminal and a ground terminal.

According to a further aspect, the housing has a lip extending around the opening to engage the electronic module and retain the electronic module in the chamber.

According to yet another aspect, the housing includes a receptacle at least partially defining the chamber and a carrier connected to the receptacle and configured to support the interface to be accessible from within the chamber. In one configuration, the carrier includes a recess and the magnet is mounted within the recess adjacent to the chamber. In another configuration, the magnet is mounted between the carrier and the receptacle, such that the carrier and the receptacle engage the magnet to retain the magnet in place.

Additional aspects of the disclosure relate to a housing that includes a receptacle having a plurality of walls defining a chamber and having an opening through at least one of the walls providing access to the chamber, an interface having a plurality of electrical contacts exposed within the chamber, and a magnet is connected to the housing. The receptacle is configured to removably receive an electronic module within the chamber by insertion of the electronic module through the opening, and the interface is configured for removable electronic connection to a connector of the electronic module when the electronic module is received in the chamber. The magnet is positioned and/or configured such that a magnetic field of the magnet penetrates the chamber.

According to one aspect, the magnet is embedded within the housing and is not physically exposed to the chamber.

According to another aspect, the housing also includes a carrier connected to the receptacle and configured to support the contacts of the interface to be exposed within the chamber. In one configuration, the carrier includes a recess and the magnet is mounted within the recess adjacent to the chamber. In another configuration, the magnet is mounted between the carrier and one of the walls of the receptacle, such that the carrier and the receptacle engage the magnet to retain the magnet in place.

According to a further aspect, the receptacle has a plurality of walls defining the chamber, and the magnet is mounted on an outer surface of one of the plurality of walls.

Other aspects of the disclosure relate to a system that includes the housing as described herein and the electronic module, where the electronic module has a sensor configured to sense the magnet when the electronic module is received in the chamber. The electronic module is configured to deactivate the connector when the sensor does not sense the magnet, and the electronic module is configured to activate the connector when the sensor does sense the magnet.

Further aspects of the disclosure relate to a system that includes an electronic module and a housing defining a chamber and having an opening providing access to the chamber such that the electronic module is configured to be removably inserted into the chamber through the opening. The electronic module includes a casing containing at least a power supply and a connector in communication with the power supply, where the connector is a USB-format connector having a plurality of connection terminals, and the USB-format connector is configured for communication with a computer device by insertion into a USB port connected to the computer device. The housing has an interface configured for removable electronic connection to the connector of the electronic module when the electronic module is received in the chamber. The interface of the housing includes a power contact and a ground contact exposed within the chamber, where the power contact engages a first terminal of the plurality of connection terminals of the USB-format connector, and the ground contact engages a second terminal of the plurality of connection terminals of the USB-format connector, such that the power supply of the electronic module is configured to supply power through the power contact and the ground contact via the first terminal and the second terminal. The plurality of connection terminals of the USB-format connector includes further terminals not engaged by the interface.

According to one aspect, the plurality of connection terminals of the USB-format connector includes four connection terminals.

According to another aspect, the electronic module further includes a computer component contained in the casing and configured for communication through the USB-format connector.

According to a further aspect, the housing includes a lip extending around the opening to engage the electronic module and retain the electronic module in the chamber.

According to yet another aspect, the housing includes a receptacle at least partially defining the chamber and a carrier connected to the receptacle and configured to support the interface to be accessible from within the chamber. In one configuration, the carrier has a first slot and a second slot that is parallel to and alongside the first slot, and the power contact and the ground contact are in the form of contact springs. In this configuration, the power contact is positioned within the first slot and the ground contact is positioned within the second slot, such that the first and second slots provide room for the power contact and the ground contact to flex upward when engaged by the connector.

According to a still further aspect, the system also includes a wearable article, where the housing is connected to and supported by the wearable article. The wearable article includes an electrically powered component and conductive leads connecting the electrically powered component to the power contact and the ground contact of the system, such that the electronic module powers the electrically powered component through the conductive leads when the electronic module is received in the chamber.

Still further aspects of the disclosure relate to a system that includes a wearable article configured to be worn on a user's body, a light emitting device or other electrically powered component mounted on the wearable article, a housing mounted on the wearable article and defining a chamber and having an opening providing access to the chamber, and an electronic module configured to be removably inserted into the chamber through the opening. The housing has an interface with electrical contacts exposed within the chamber, and a plurality of electrical leads connect the light emitting device to the electrical contacts of the interface of the housing. The electronic module includes a casing containing at least a power supply and a connector in communication with the power supply, and the connector of the electronic module is configured for removable electronic connection to the electrical contacts of the interface when the electronic module is received in the chamber. The electronic module is configured for providing power from the power supply to the light emitting device through the interface and the electrical leads when the electronic module is received in the chamber.

According to one aspect, the connector of the electronic module is a USB-format connector, and the electronic module further includes a computer component contained in the casing and configured for communication through the USB-format connector.

According to another aspect, the housing includes a lip extending around the opening to engage the electronic module and retain the electronic module in the chamber.

According to a further aspect, the housing includes a receptacle at least partially defining the chamber and a carrier connected to the receptacle and configured to support the interface to be accessible from within the chamber.

According to yet another aspect, the housing has a flange extending outwardly around a periphery of the housing and a central portion defining the chamber and the opening, where the wearable article is connected to the housing around the flange, and the central portion is open and accessible from an exterior of the wearable article.

According to a still further aspect, the housing is connected to the wearable article by a bonding material.

Other features and advantages of the disclosure will be apparent from the following description taken in conjunction with the attached drawings.

BRIEF DESCRIPTION OF THE DRAWINGS

To allow for a more full understanding of the present invention, it will now be described by way of example, with reference to the accompanying drawings in which.

DETAILED DESCRIPTION

Figure 1:
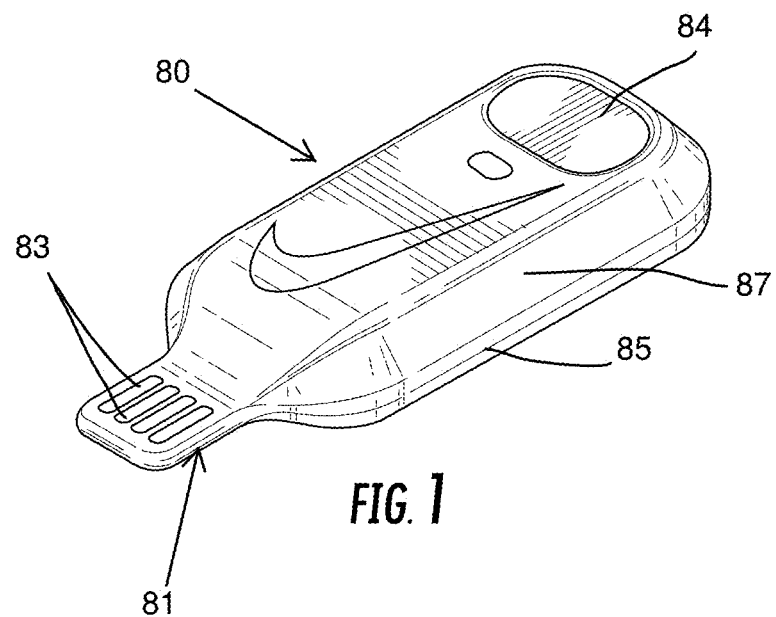
FIG. 1 is a top front perspective view of one embodiment of an electronic module according to aspects of the present disclosure.

In the following description of various example structures according to the invention, reference is made to the accompanying drawings, which form a part hereof, and in which are shown by way of illustration various example devices, systems, and environments in which aspects of the invention may be practiced. It is to be understood that other specific arrangements of parts, example devices, systems, and environments may be utilized and structural and functional modifications may be made without departing from the scope of the present invention. Also, while the terms "top," "bottom," "front," "back," "side," "rear," "primary," "secondary," and the like may be used in this specification to describe various example features and elements of the invention, these terms are used herein as a matter of convenience, e.g., based on the example orientations shown in the figures or the orientation during typical use. Additionally, the term "plurality," as used herein, indicates any number greater than one, either disjunctively or conjunctively, as necessary, up to an infinite number. Nothing in this specification should be construed as requiring a specific three dimensional orientation of structures in order to fall within the scope of this invention. Also, the reader is advised that the attached drawings are not necessarily drawn to scale.

The following terms are used in this specification, and unless otherwise noted or clear from the context, these terms have the meanings provided below.

"Providing" a component, as used herein, refers broadly to making an article available or accessible for future actions to be performed on the article, and does not connote that the party providing the article has manufactured, produced, or supplied the article or that the party providing the article has ownership or control of the article.

This application incorporates by reference U.S. patent application Ser. No. 13/828,893, filed Mar. 14, 2013; U.S. patent application Ser. No. 14/946,682, filed Nov. 19, 2015; U.S. patent application Ser. No. 14/946,670, filed Nov. 19, 2015; U.S. patent application Ser. No. 14/946,674, filed Nov. 19, 2015; U.S. patent application Ser. No. 14/946,691, filed Nov. 19, 2015; U.S. Provisional Application No. 62/082,113, filed Nov. 19, 2014; U.S. Provisional Application No. 62/100,782, filed Jan. 7, 2015; U.S. Provisional Application No. 62/146,029, filed Apr. 10, 2015; U.S. Provisional Application No. 62/168,357, filed May 29, 2015; U.S. Provisional Application No. 62/168,502, filed May 29, 2015; U.S. Provisional Application No. 62/215,497, filed Sep. 8, 2015; U.S. Provisional Application No. 62/359,879, filed Jul. 8, 2016; and U.S. Provisional Application No. 62/356,960, filed Jun. 30, 2016.

In general, aspects of this disclosure relate to a housing 20 configured for connection with an article of apparel 10, where the housing 20 removably engages an electronic module 80, as well as a system 12 that includes the housing 20 and/or the article of apparel 10 in combination with the electronic module 80, where the electronic module 80 is configured for various functionality with respect to the article of apparel 10 and/or the user. In one embodiment, the article of apparel 10 includes one or more electrically-powered components 14, and the functionality of the electronic module 80 includes powering the electrically-powered component(s) 14. The housing 20 and/or the article of apparel 10 in this embodiment include various connection structures to establish an electrical connection between the housing 20 and the electrically-powered component(s) 14 to allow the module 80 to power the component(s) 14 when engaged with the housing 20.

Figure 16:
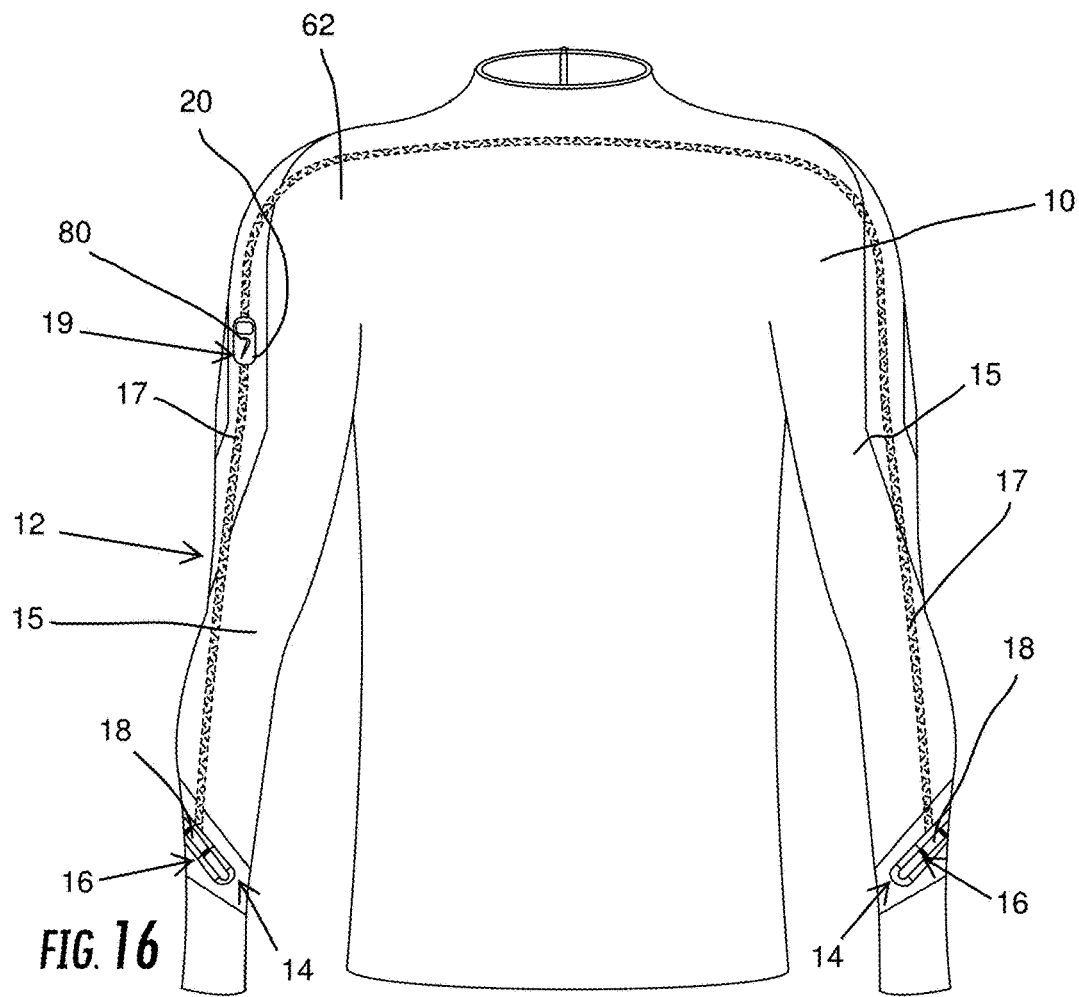
FIG. 16 is a rear view of one embodiment of a wearable article in the form of a shirt or jacket having a housing assembly connected thereto, according to aspects of the present disclosure, showing an exterior of the article.
Figure 17:
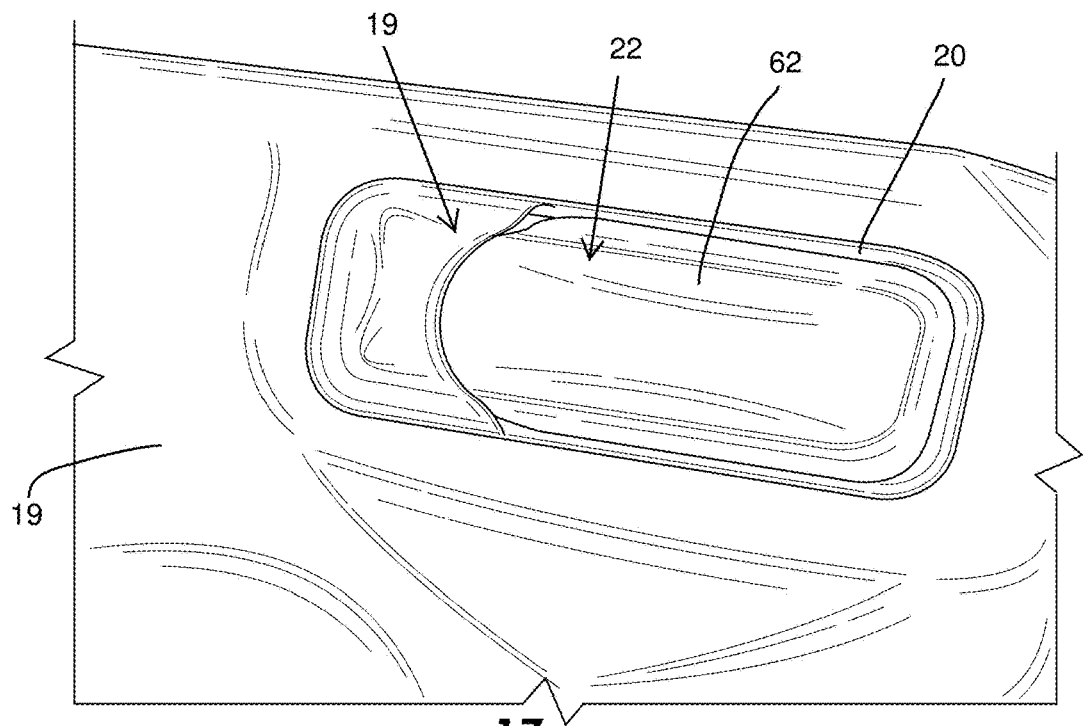
FIG. 17 is a plan view of the housing assembly and a portion of the exterior of the wearable article of FIG. 16.
Figure 18:
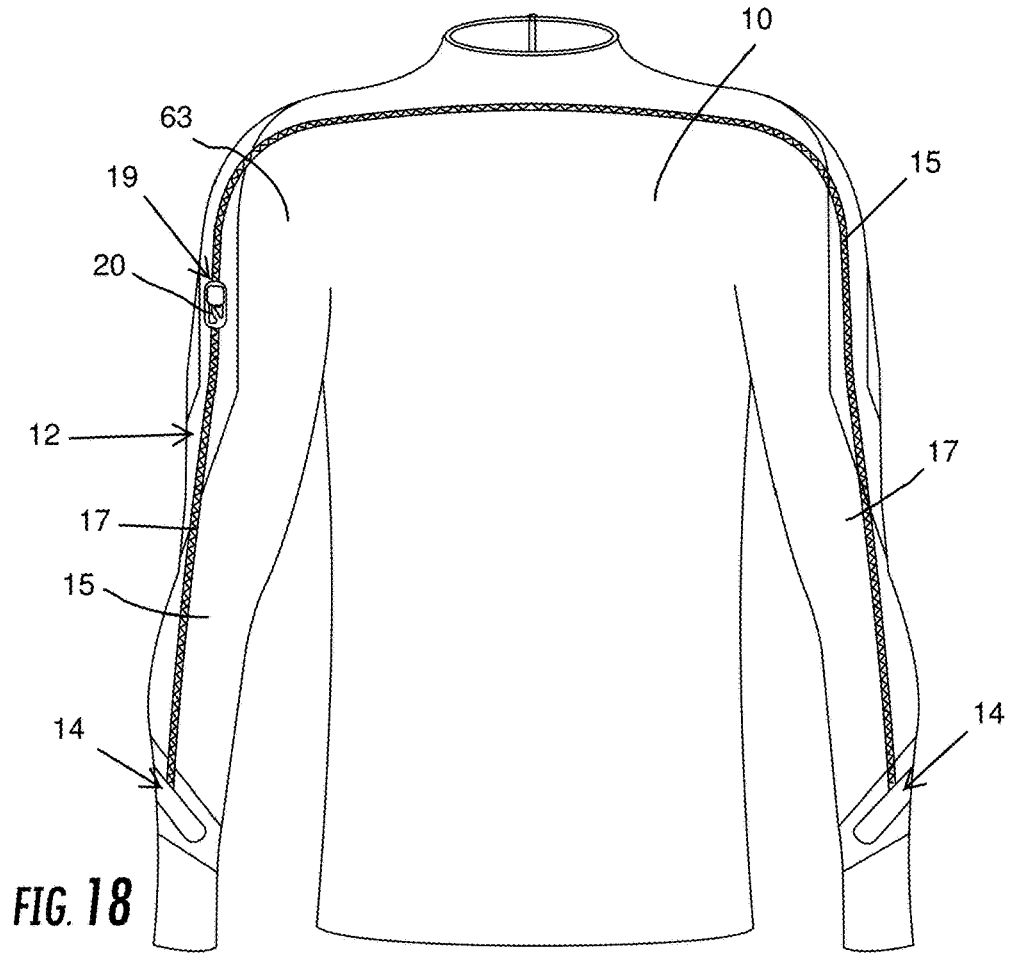
FIG. 18 is a rear view of the wearable article and the housing assembly of FIG. 16, shown inside out to illustrate an interior of the article.

An example of an article of apparel 10 is shown in FIGS. 16-18 in the form of an upper body garment (e.g., a shirt or jacket) having the housing 20 mounted on the article 10 and positioned in the shoulder region. It is understood that the housing 20 and other aspects described herein may be used with any article of apparel 10, including traditional articles of apparel such as shirts, pants, bodysuits, outerwear, footwear, hats, gloves, belts, etc., or specialized articles of apparel that are designed specifically to support the housing 20, such as armbands, waistbands, harnesses, or other wearable articles. In one embodiment, the article 10 has at least one electrically-powered component 14 connected thereto. The article 10 illustrated in FIGS. 16-18 includes an electrically-powered component 14 in the form of one or more arrays 16 of light emitting devices 18, e.g., light-emitting diodes (LEDs) or other devices. The article 10 has arrays 16 located on the forearm area of each arm portion 15 in FIGS. 16-18. A pair of conductive leads 17 (e.g., +/− or power/ground) are connected to each array 16 and are configured to supply power to all of the light emitting devices 18 of the array 16. The leads 17 in the embodiment of FIGS. 16-18 are configured in a wave or zig-zag pattern and are mounted on an elastically deformable material. This configuration permits stretching and flexing of the leads 17 without damage, which is advantageous when the leads 17 extend across an area of the article 10 that moves or flexes during use. The leads 17 extend to a power source for powering the array 16 or other electrically-powered component 14, and in the embodiment of FIGS. 16-18, the leads 17 extend to the housing 20 to permit the module 80 to serve as the power supply. The electrically-powered component 14 may be configured as shown and described in U.S. patent application Ser. No. 13/828,893; U.S. Provisional Application No. 62/359,879; and/or U.S. Provisional Application No. 62/356,960. It is understood that the article of apparel 10 may be considered to be part of an assembly including the article 10 as well as the component 14, the housing 20, and other features.

One example embodiment of the housing 20 is illustrated in FIGS. 2-13. The housing 20 is formed separately from the article 10 and is connected to the article 10, such as by bonding, mechanical connections, or combinations thereof. The housing 20 is configured for engaging and retaining the module 80 and may be provided as part of a housing assembly 19 that includes the housing 20 along with electrical connecting structure 30 that forms an interface 31 configured for electronic connection to the module 80 when the module 80 is engaged with the housing 20. In the embodiment of FIGS. 2-13, the housing 20 comprises a receptacle 21 that defines a chamber 22 configured for receiving the module 80, but the housing 20 may engage and retain the module 80 using a different structure in another embodiment. The housing 20 may be made of a thermoplastic polyurethane (TPU) material and formed by injection molding in one embodiment, but may be partially or completely made from other materials and/or other techniques in other embodiments. In one embodiment, the receptacle 21 is formed of a single piece by injection molding. The receptacle 21 in this embodiment is a moderately rigid shell that has walls 23 defining the chamber 22 and also has an access opening 24 providing access to the chamber 22. In one embodiment, the rigidity of the receptacle 21 may be sufficient to protect the module 80. The rigidity of the material forming the receptacle 21 may be greater than the rigidity of the material forming the article 10. As shown in FIGS. 2-5, the receptacle 21 in the illustrated embodiment has a lip 25 that extends inwardly around at least a portion of the access opening 24 and functions to retain the module 80 within the chamber 22. The walls 23 of the receptacle 21 are configured to enclose and hold a portion of the module 80 (e.g., a connector 81), as described in greater detail herein. In the embodiment of FIGS. 2-5, a one of the walls 23 extends over the top side 27 of the receptacle 21 to form this enclosure, such that the wall 23 and the lip 25 define the access opening 24 on the top side 27.

In one embodiment, the housing 20 further has a flange 26 that extends outwardly around at least a portion of the periphery of the receptacle 21 and is configured for connection to the article 10. In the embodiment shown in FIGS. 2-13, the flange 26 extends generally in a single plane around the entire periphery of the receptacle 21. In other embodiments, the flange 26 may have a different configuration (e.g., intermittent), or may not be present. Generally, the exterior surfaces of the housing 20 shown in FIGS. 2-13 are smoothly contoured, both for aesthetics and for increased comfort when the housing 20 engages the user's body. The housing 20 also has a bottom side 28 opposite the top side 27. In the embodiment of FIGS. 2-13, a wall 23 forms the majority of the bottom side 28 with a second opening or cavity opening 29 defined in the bottom side to permit the electrical connecting structure 30 to enter the housing 20 to connect with the interface 31.

Figure 11:
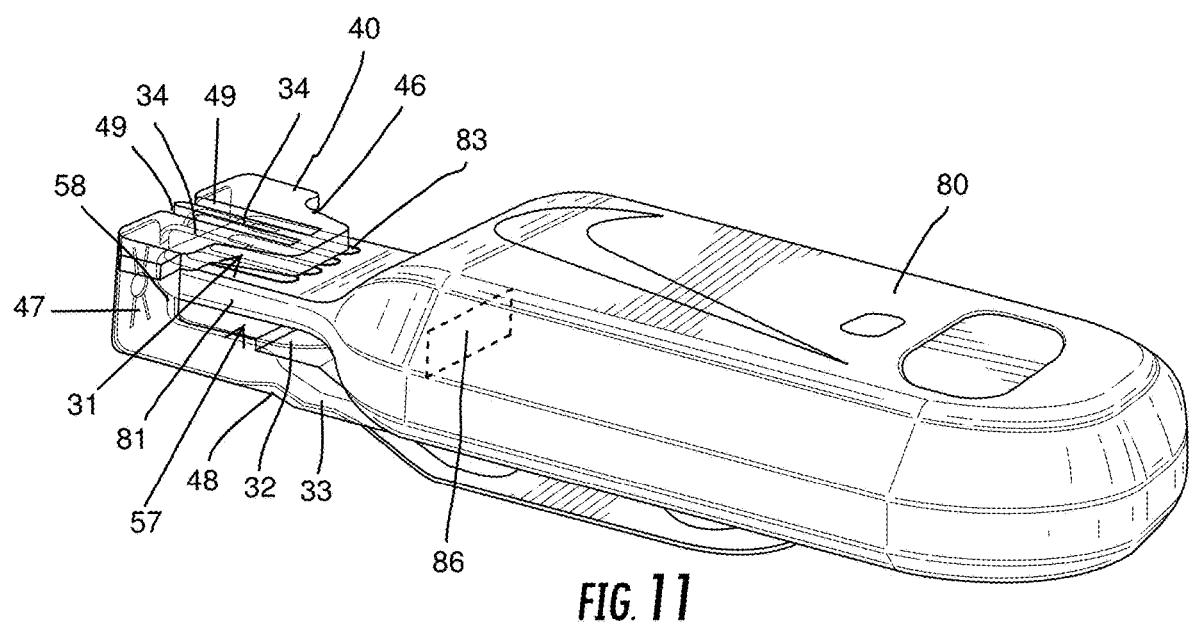
FIG. 11 is a top rear perspective view of the module of FIG. 1 engaged with the carrier and contact members of FIG. 8, with the carrier and the contact members being shown partially transparent.
Figure 12A:
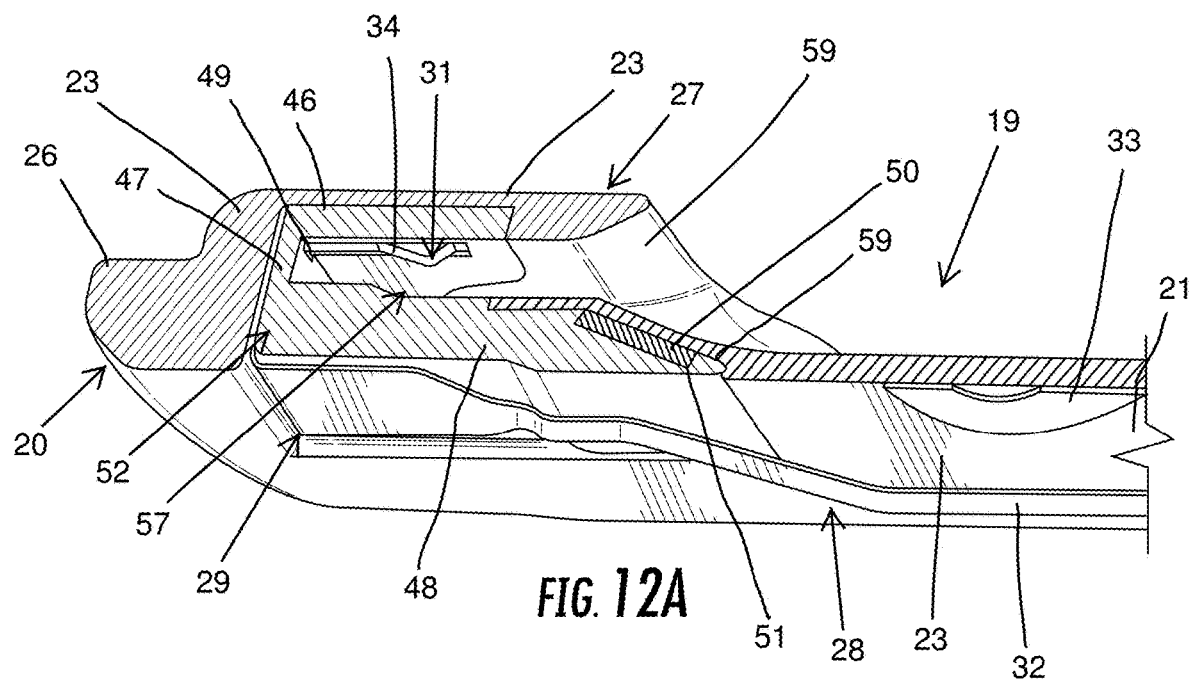
FIG. 12A is a partial longitudinal cross-sectional view of the housing assembly of FIG. 6.
Figure 12B:
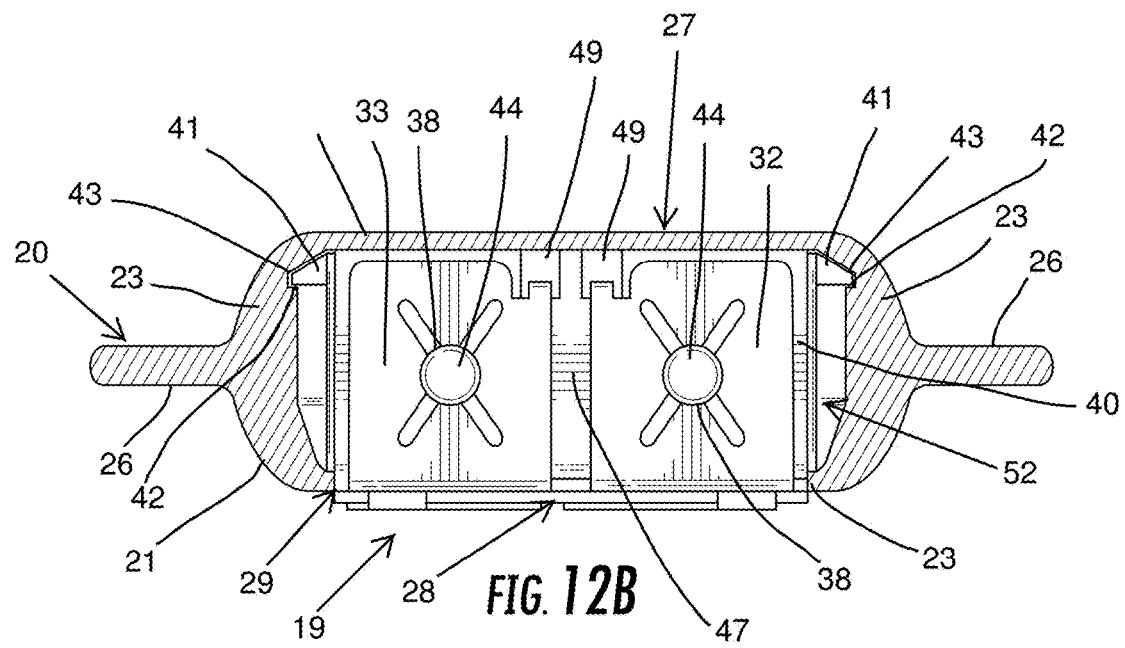
FIG. 12B is a lateral cross-sectional view of the housing assembly of FIG. 6.

In one embodiment, the housing 20 further includes a carrier 40 that is connected to the receptacle 21 and holds and supports a portion of the electrical connecting structure 30 to be exposed to the chamber 22 to form the interface 31. The carrier 40 is formed as a separate piece from the receptacle 21 in the embodiment of FIGS. 2-13, and is connected to the receptacle 21 by a mechanical engaging structure. The carrier 40 in this embodiment has two retaining tabs 41 that extend outwardly from the lateral sides of the carrier 40 and engage engagement surfaces 42 located on the inner sides of the walls 23 on the lateral sides of the receptacle 21 to retain the carrier 40 in connection with the receptacle 21. This engagement is shown in FIG. 12B, where the engagement surfaces 42 are defined within slots 43 on the walls 23 of the receptacle 21, in which the tabs 41 are received. In this embodiment, the carrier 40 is inserted through the cavity opening 29 on the bottom side 28 of the receptacle 21 until the tabs 41 are received in the slots 43, and the tabs 41 have ramped surfaces to aid this insertion. It is understood that additional connecting structures may be used in this embodiment, including other mechanical engaging structures (including separate connectors or fasteners) and/or other types of connecting structures, such as welding, bonding, etc. In other embodiments, the carrier 40 may be connected to the receptacle 21 using a different connecting structure and/or technique, including any structure described above or combinations of such structures.

The carrier 40 is at least partially received in a cavity 52 inside the receptacle 21 that is in communication with the chamber 22, permitting the carrier 40 to position the electrical contacts 34 to be exposed to the chamber. The structure of the carrier 40 includes a shelf 46 that extends into the chamber 22, with the carrier 40 having slots 49 that extend through the shelf 46 to accommodate the electrical contacts 34. The carrier 40 also includes a column 47 that depends from the rear end of the shelf 46 and a base 48 that extends forward from the column 47, such that the carrier 40 has a C-shape, as shown in FIGS. 10-12A. The connector 81 of the module 80 may be received between the shelf 46 and the base 48 when the module 80 is received in the chamber 22 in one embodiment, as illustrated in FIG. 11. Additionally, a portion of the base 48 in the embodiment of FIGS. 2-13 extends farther forward and fits with the receptacle 21 to extend below a wall of the receptacle 21, as shown in FIG. 12A. This configuration creates a more balanced and multi-point connection between the carrier 40 and the receptacle 21. In further embodiments, the carrier 40 may have a different structure, and/or the carrier 40 may be integrally formed with the receptacle 21 or with a portion of the receptacle 21, such that the carrier 40 is not a separate piece.

Further structure of the carrier 40 for supporting portions of the electrical connecting structure 30 is described in greater detail below.

The electrical connecting structure 30 generally creates a pathway for electrical connection of an external component (e.g., the electrically powered component 14 and/or the leads 17) to the module 80 when the module 80 is engaged with the housing 20. In the embodiment of FIGS. 2-13, the electrical connecting structure 30 includes two contact members 32, 33 that are separate from each other and have portions exposed within the chamber 22 to form electrical contacts 34 of the interface 31. It is understood that the number of contact member 32, 33 may be the same as the number of active terminals 83 on the module 80. For example, the interface 31 in FIGS. 2-13 has two electrical contacts 34 (power/ground or +/−), and the connector 81 has two active terminals 83, as described in greater detail below. The contact members 32, 33 illustrated in FIGS. 2-13 each includes a contact pad 35 configured to be connected to an external component (e.g., the leads 17) and an arm 36 that extends from the contact pad 35 into the chamber 22 to form an electrical contact 34. In one embodiment, the arms 36 and the contact members 32, 33 themselves each form a 180° bend between the contact pads 35 and the electrical contacts 34, as shown in FIGS. 7-8, where the arms 36 extend along the bottom side 28 of the receptacle 21, then upward into the receptacle 21, and then back into the chamber 22 to form the electrical contacts 34. The contacts 34 in this embodiment are configured as contact springs that extend into the chamber 22 and exert a downward force on the connector 81 to maintain secure contact, while being able to flex upward to accommodate the shape of the connector 81, but may be differently configured in other embodiments. The contact members 32, 33 in one embodiment may each be made from a single blank of sheet metal material, which is formed into the contact member 32, 33 by various forming operations, such as cutting, stamping, punching, bending, etc. This enables the contact members 32, 33 to be manufactured quickly and easily at low cost. In other embodiments, the contact members 32, 33 may be formed of a different material and/or by a different technique.

Figure 6:
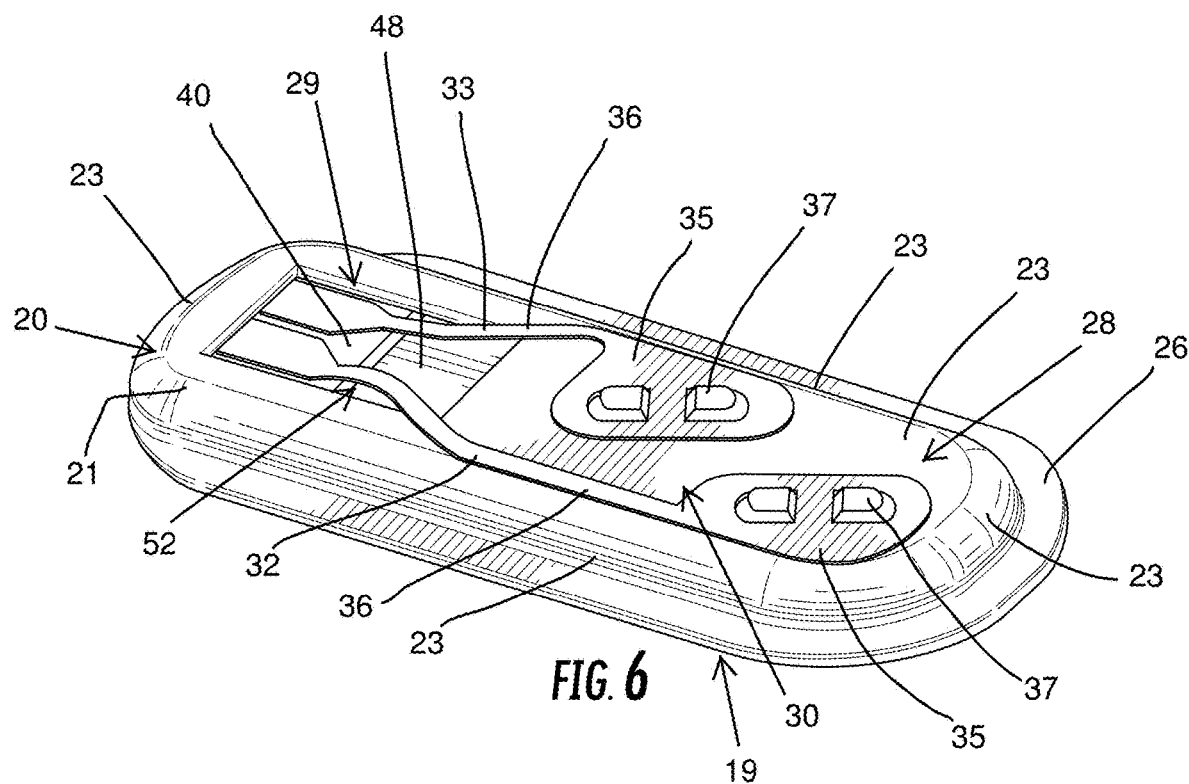
FIG. 6 is a bottom rear perspective view of one embodiment of a housing assembly including the housing of FIG. 2, according to aspects of the present disclosure.
Figure 7:
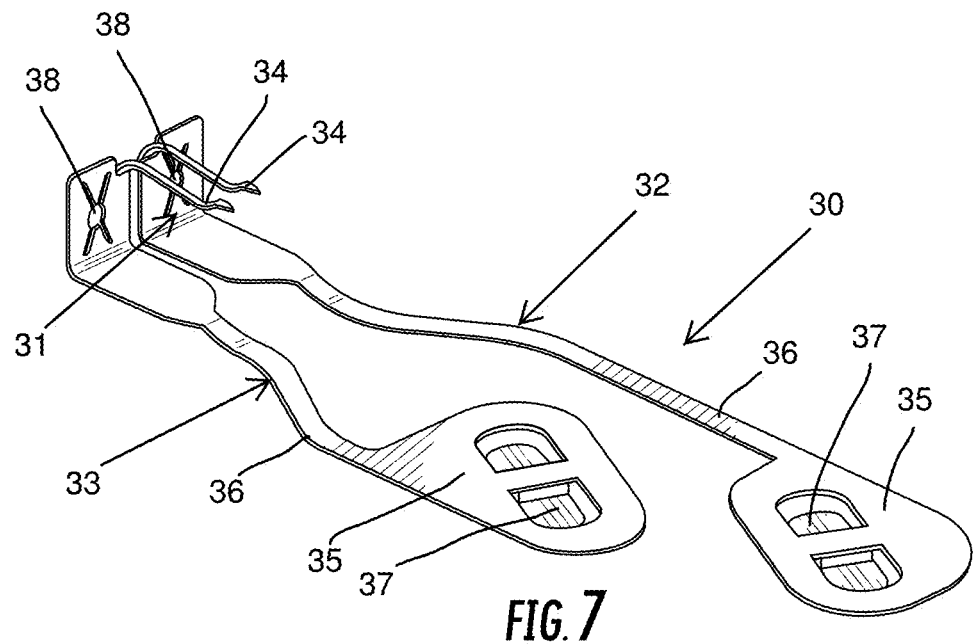
FIG. 7 is a top rear perspective view of one embodiment of a pair of electrical contact members of the housing assembly of FIG. 6, according to aspects of the present disclosure.
Figure 8:
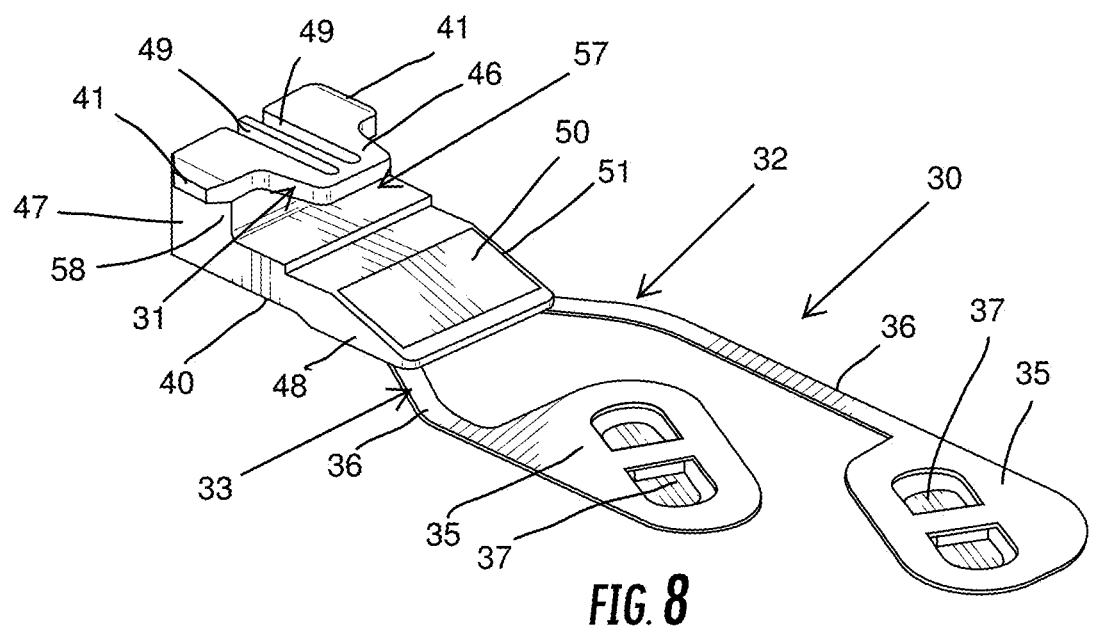
FIG. 8 is a top rear perspective view of one embodiment of a carrier of the housing assembly of FIG. 6 engaged with the contact members, according to aspects of the present disclosure.
Figure 9:
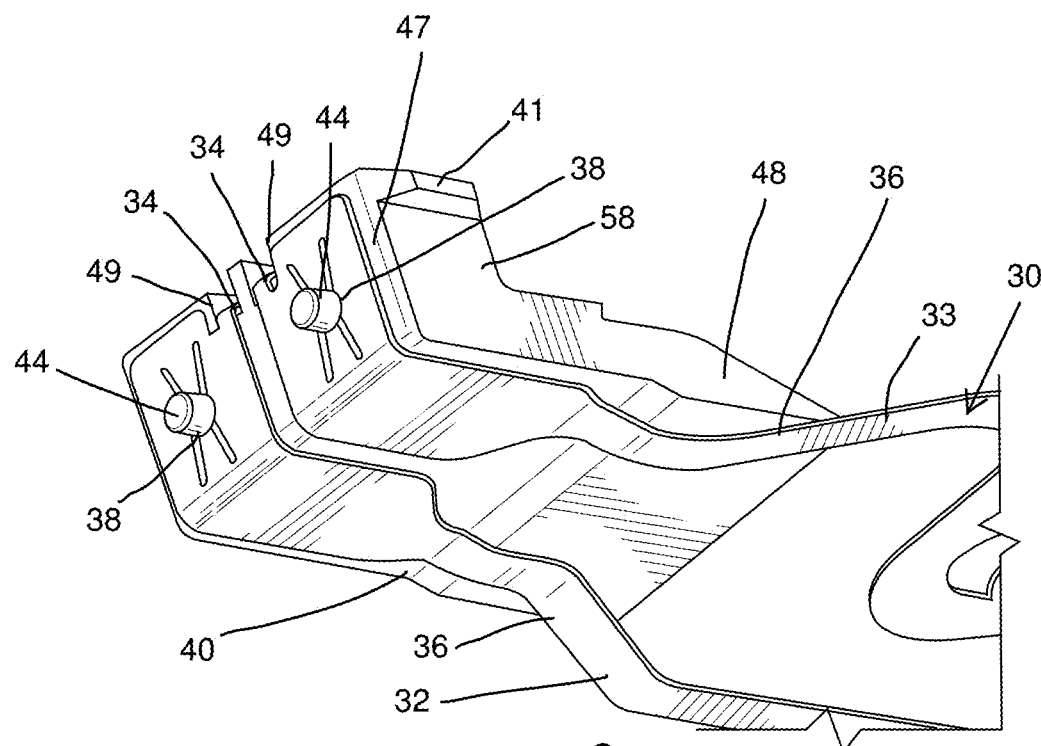
FIG. 9 is a partial bottom front perspective view of the carrier and the contact members of FIG. 8.
Figure 10:
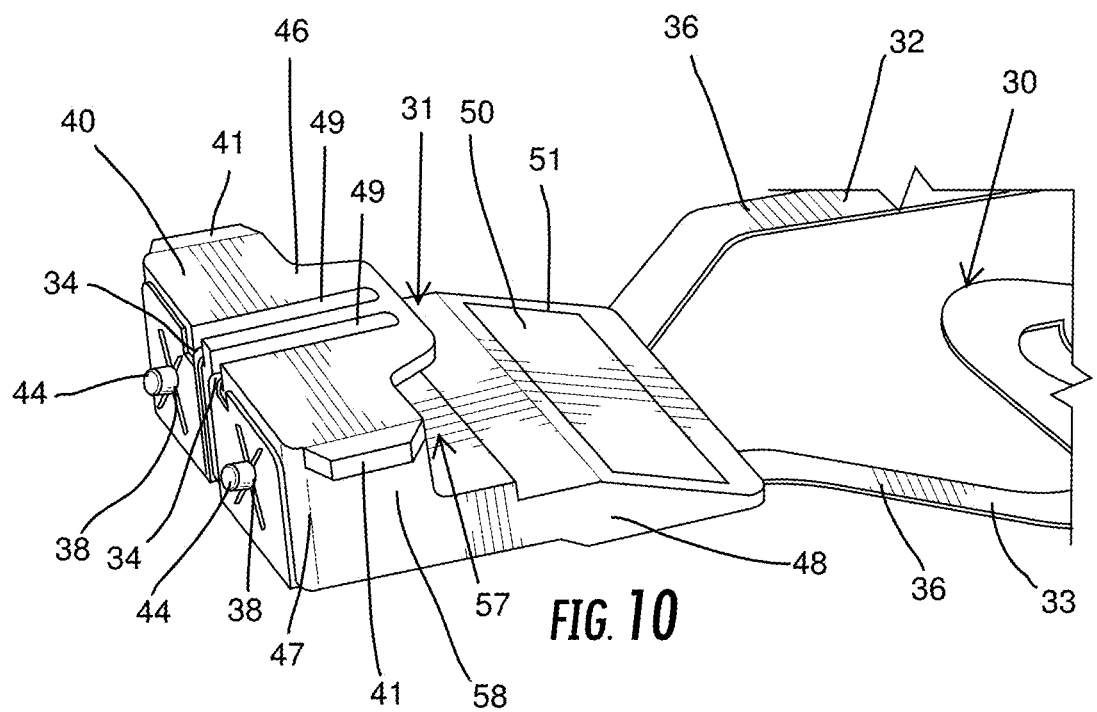
FIG. 10 is a partial top front perspective view of the carrier and the contact members of FIG. 8.

The contact pads 35 are shown in FIGS. 6-8 as having enlarged widths relative to the arms 36, providing a large surface for connection of a lead 17 or other external component. Connection of the leads 17 to the contact pads 35 places the leads 17 and the component(s) to which the leads 17 are connected in communication with the contact members 32, 33, and thereby in communication with the interface 31. As shown in FIG. 6, the contact pads 35 may have a width that is greater than half the width of the bottom side 28 of the receptacle 21, and the contact pads 35 are staggered with overlapping widths and have structure (e.g., angled surfaces) to provide maximum contact area within the boundaries of the bottom side 28 of the receptacle 21.

Figure 14:
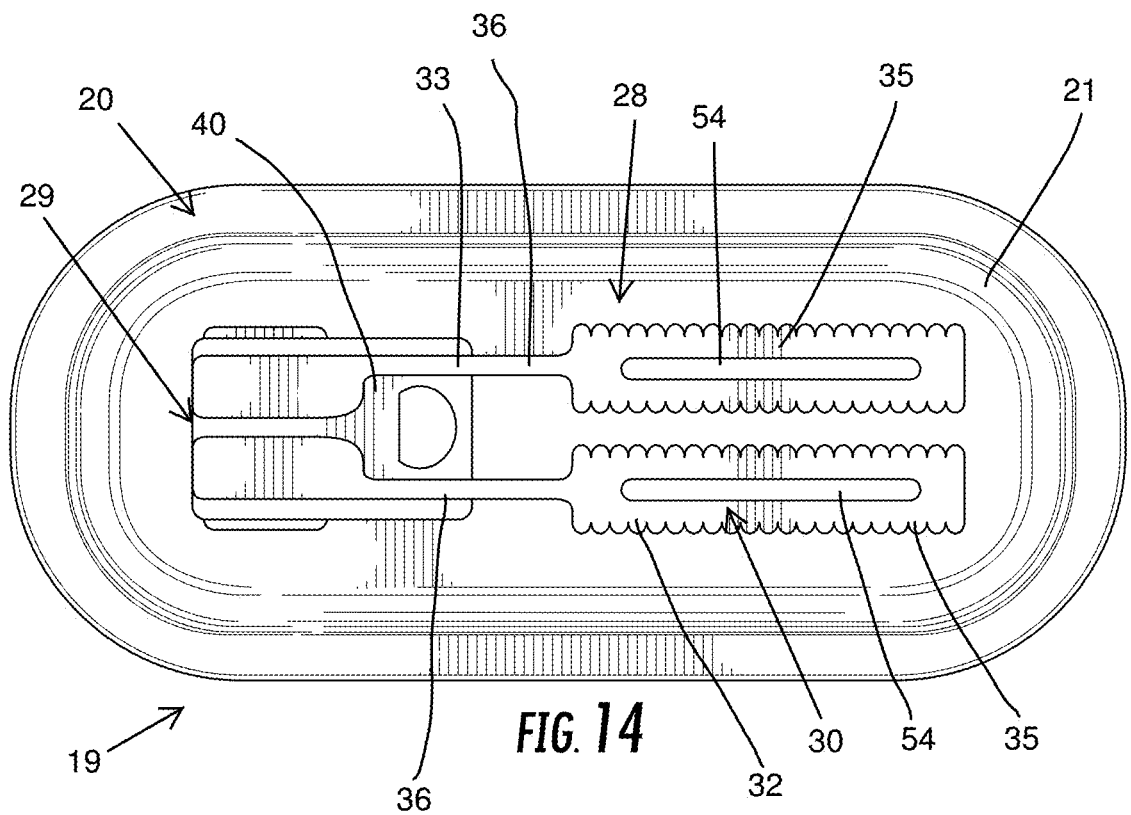
FIG. 14 is a bottom view of another embodiment of a housing assembly according to aspects of the present disclosure.
Figure 15:
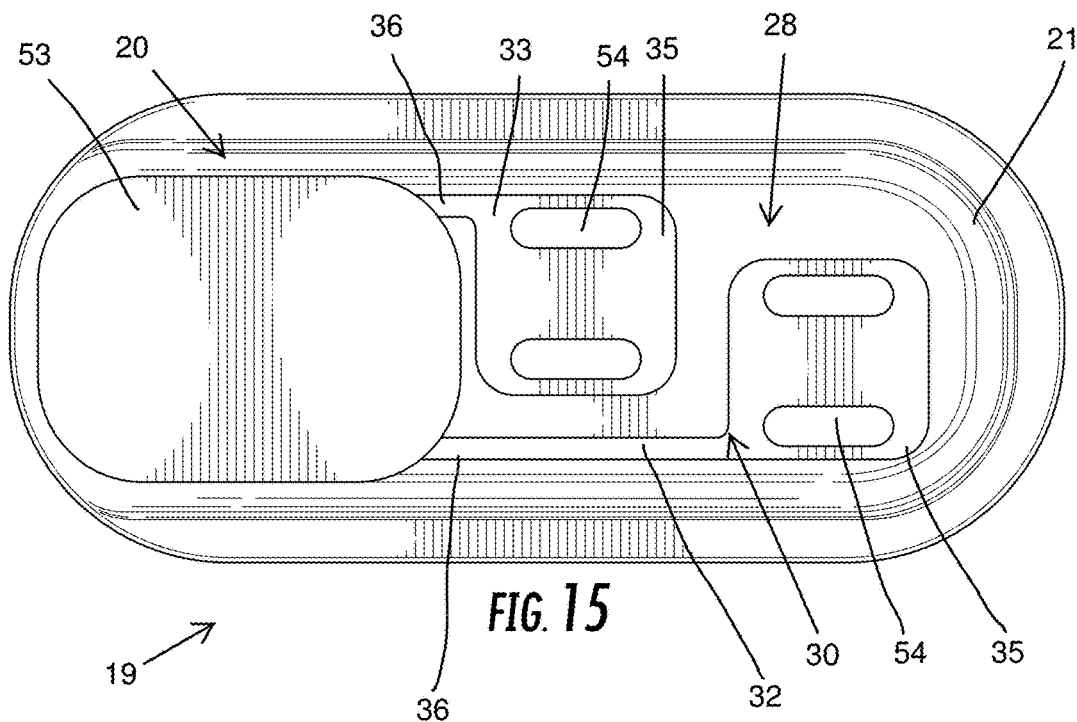
FIG. 15 is a bottom view of another embodiment of a housing assembly according to aspects of the present disclosure.
Figure 19:
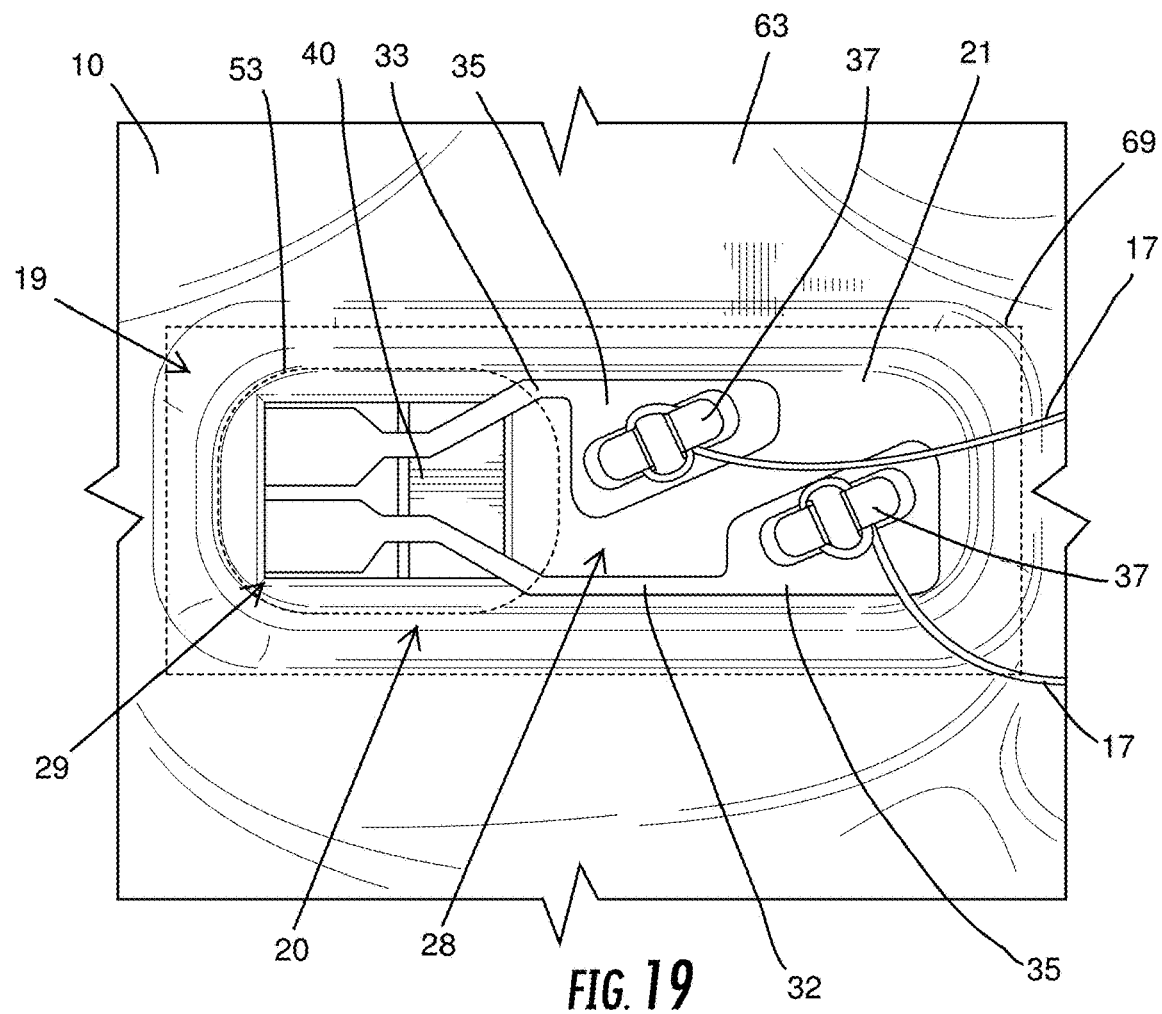
FIG. 19 is a plan view of the housing assembly and a portion of the interior of the wearable article of FIG. 16, with conductive leads connected to the housing assembly.
Figure 26:
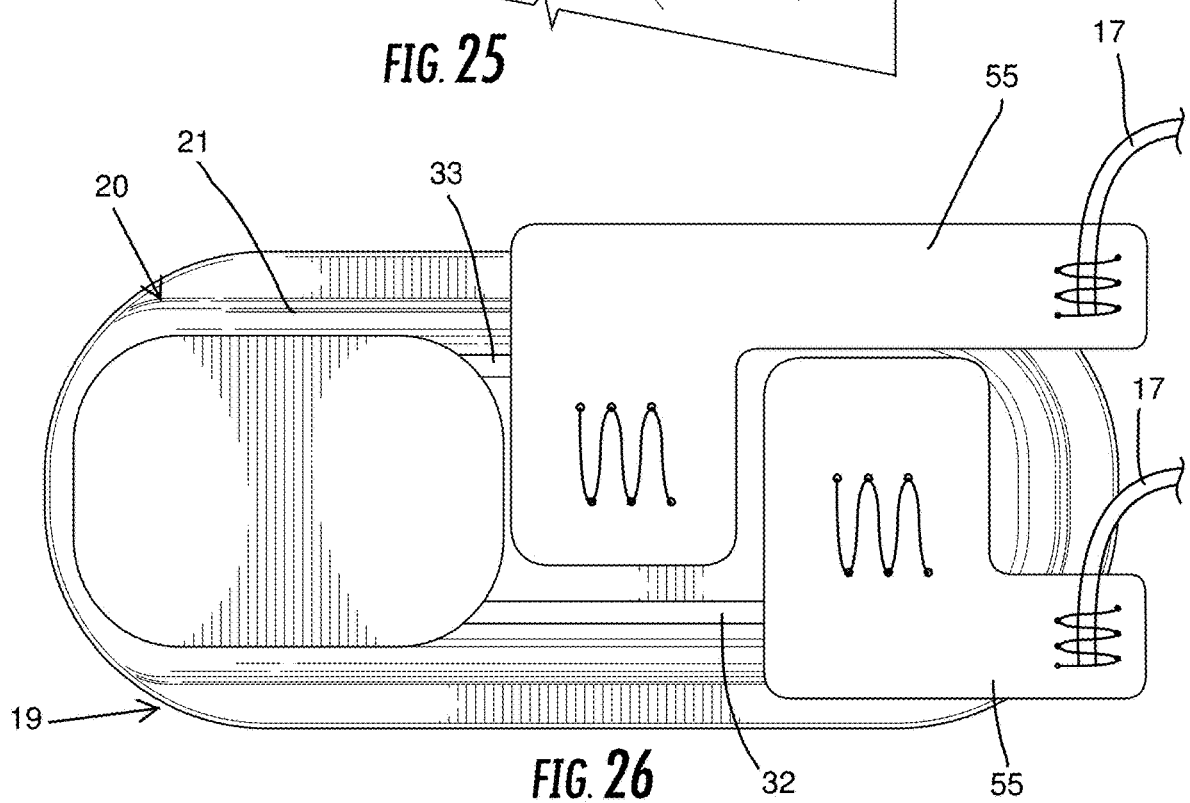
FIG. 26 is a bottom view of another embodiment of a housing assembly according to aspects of the present disclosure, with conductive leads connected to the housing assembly.

The contact pads 35 may be configured for connection to the leads 17 using various different structures, which may be more particularly suited to connection to a specific type of lead 17 (e.g., wire, fabric, thread, conductive trace, etc.). The contact pads 35 may each have at least one projection 37 for connection of a lead 17 by winding around the projection(s) 37 in one embodiment. In the embodiment of FIGS. 2-13, each contact pad 35 has two projections 37, and the leads 17 are connected by winding around both projections 37, as shown in FIG. 19. In other embodiments, the contact pads 35 may be located in a different location and may have any structure that functions to form a connection with an external component. For example, the contact pads 35 in FIG. 14 have a ridged structure with a central slot 54, which permits winding of leads 17 around the exterior (e.g., wire leads) or threading of the leads 17 through the slot 54 (e.g., sewing conductive thread leads). As another example, the contact pads 35 in FIG. 15 have a pair of slots 54, which can permit winding of the leads 17 between the slots 54 or threading the leads 17 through both slots 54. As a further example, the leads 17 can be connected to intermediate conductors 55, as shown in FIG. 26, which are then connected to the contact members 32, 33. In the embodiment of FIG. 26, the leads 17 are conductive thread leads, and the intermediate conductors 55 are pieces of a conductive fabric. The leads 17 in this configuration are sewn/stitched to the intermediate conductors 55, which are then sewn/stitched to the contact pads 35 of the two contact members 32, 33, which may be configured as shown in FIG. 15. In other embodiments, other types and configurations of intermediate conductors 55 may be used, including in connection with leads 17 and/or contact members 32, 33 that are differently configured. It is understood that the contact members 32, 33 in the embodiments of FIGS. 14-15 and 26 may be otherwise configured substantially similarly to the contact members 32, 33 in FIGS. 2-13 or according to any other embodiment described herein.

As illustrated in FIGS. 6 and 12A, the contact pads 35 in this embodiment are external to the housing 20, being positioned adjacent the bottom side 28 of the receptacle 21, and the arms 36 extend from the exterior of the housing 20 through one of the walls 23 of the receptacle 21 (e.g., through the cavity opening 29) and into the chamber 22. Additionally, the contact members 32, 33 each have a mounting structure for connection to the housing 20 in one embodiment. As shown in the embodiment of FIGS. 7-12B, the carrier 40 has two posts 44 on the rear surface, and the arms 36 of the contact members 32, 33 each have a receiver 38 that receives one of the posts 44. The portions of the arms 36 surrounding the receivers 38 are enlarged, and the receivers 38 are configured for receiving the posts 44 in a press-fit connection in this embodiment. It is understood that in one embodiment, the contact members 32, 33 may be provided with a greater number of connection and/or bracing points to hold the contact members 32, 33 in place after complete assembly, and that the mounting structure (e.g., posts 44 and receivers 38) may be used to connect the contact members 32, 33 to the carrier 40 during assembly and prior to connection of the carrier 40 to the receptacle 21 in one embodiment. The contact members 32, 33 may have additional or different mounting structure in other embodiments.

Figure 22:
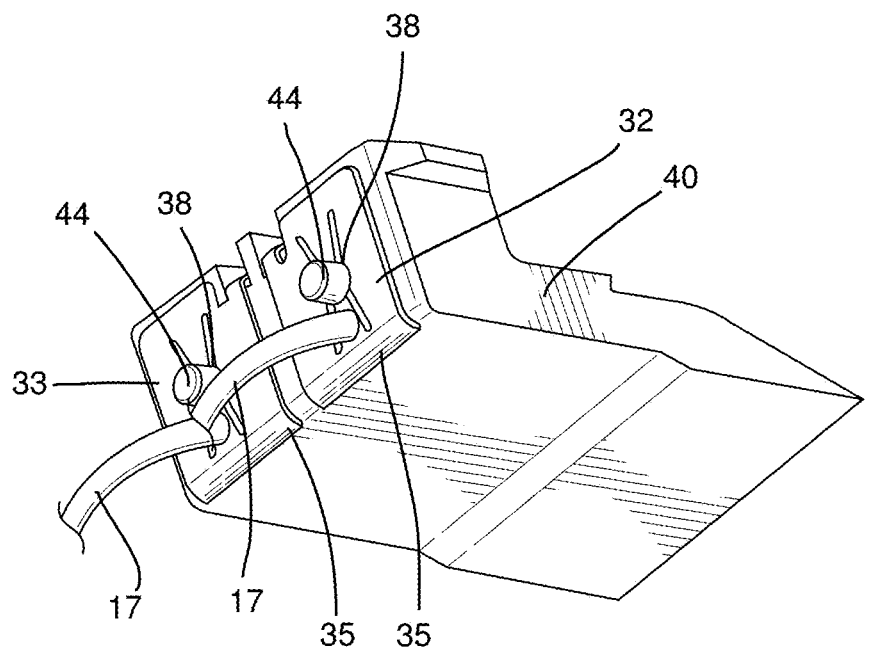
FIG. 22 is a bottom front perspective view of another embodiment of a carrier, contact members, and conductive leads according to aspects of the present disclosure.

In another embodiment, illustrated in FIG. 22, the contact members 32, 33 may have contact pads 35 that are not located on the exterior of the housing 20. In this embodiment, the contact pads 35 are located along the back wall of the carrier 40 and within the cavity 52 after assembly. As shown in FIG. 22, the electrical contacts 34 extend directly from the contact pads 35 in this embodiment. The leads 17 are shown as being welded to the contact pads 35 in FIG. 22, but the contact pads 35 may be provided with other connecting structure in other embodiments. The contact pads 35 in FIG. 22 further include mounting structure 38 for connection to the carrier 40, as described in greater detail below.

The carrier 40 is configured for positioning the electrical contacts 34 of the contact members 32, 33 in a position to be exposed to the chamber 22 of the housing 20 for connection to the module 80, in addition to the mounting structure 38, 44. In one embodiment 3, the electrical contacts 34 are received within the slots 49 in the carrier 40, as shown in FIGS. 8-12B. The arms 36 of the contact members 32, 33 in this embodiment extend along the rear surface of the carrier 40 as described above, and the slots 49 extend through to the rear of the carrier 40, such that the electrical contacts 34 extend forwardly into the slots 49 and are at least partially received in the slots 49. The slots 49 allow the electrical contacts 34 to be exposed to the chamber 22 below the shelf 46 of the carrier 40, while also providing room for the contacts 34 to flex upward if necessary when engaged by the module 80. The carrier 40 in this configuration provides both a positioning or registration function with respect to the module 80, positioning both the electrical contacts 34 and the module connector 81 in position for connection, as well as a protective function for the electrical contacts 34. The carrier 40 and/or the contact members 32, 33 may have different structures in other embodiments, and may have complementary structures to facilitate the positioning and protective functions.

In one example embodiment, the housing 20 includes a magnet 50 connected to the housing 20 and configured for interaction with the module 80 when the module 80 is engaged with the receptacle 21, as described in greater detail below. The magnet 50 is positioned so that the magnetic field of the magnet 50 penetrates the chamber 22. The housing 20 in the embodiment of FIGS. 2-13 includes a magnet 50 that is engaged with the carrier 40 and is received within a recess 51 on the carrier 40 adjacent to the chamber 22. The recess 51 is located on the distal end of the base 48, which is distal from the column 47 in the embodiment illustrated in FIGS. 8-12A. The magnet 50 in this embodiment is embedded within the housing 20 and not physically exposed to the chamber 22, with one of the walls 23 of the receptacle 21 positioned between the magnet 50 and the chamber 22 and the magnet 50 being positioned on the outer surface of the wall 23, as illustrated in FIG. 12A. The magnet 50 may be held within the recess 51 by engagement by both the carrier 40 and the adjacent wall 23 of the receptacle 21 in one embodiment. Additional or alternate retaining structures may be used in other embodiments, including a bonding material, mechanical retaining structures, fasteners, etc. In other embodiments, the magnet 50 may be integrally molded within the housing 20, such as within the carrier 40 or within a wall 23 of the receptacle 21, or the magnet 50 may be mounted on the carrier 40 using a different structure. In additional embodiments, the magnet 50 may be mounted on the receptacle 21 and/or the magnet 50 may be positioned so that at least a portion of the magnet 50 is physically exposed within the chamber 22.

Figure 13:
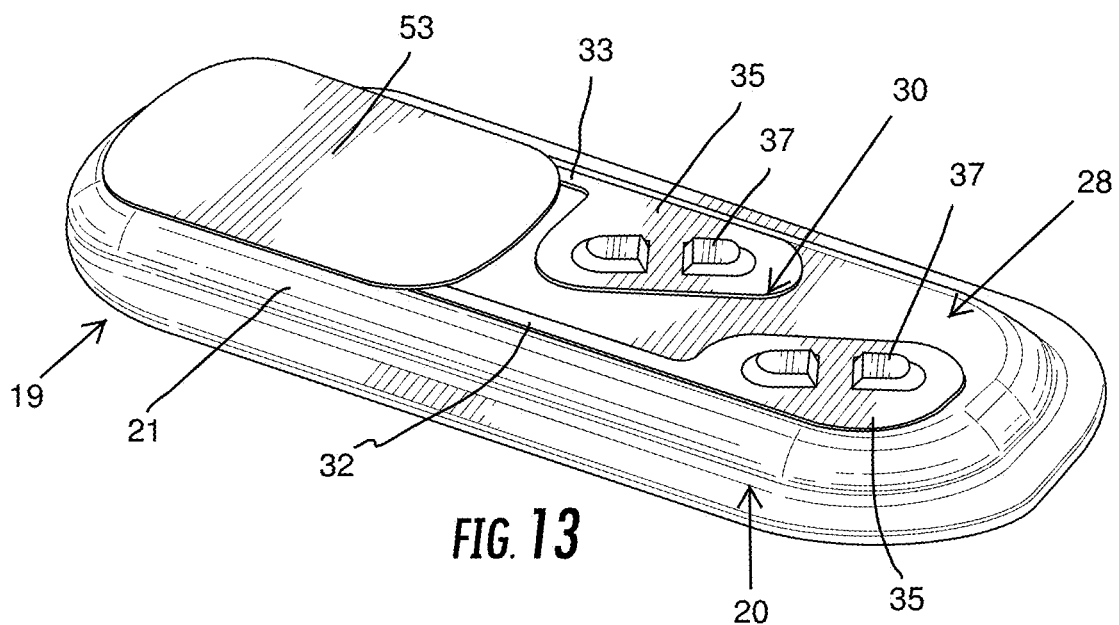
FIG. 13 is a bottom rear perspective view of the housing assembly of FIG. 6 with one embodiment of an insulative material covering a portion of the housing assembly according to aspects of the present disclosure.

The housing assembly 19 is assembled according to one embodiment by first connecting the contact members 32, 33 and the magnet 50 to the carrier 40. In the embodiment of FIGS. 2-13, the magnet 50 may be secured by placing the magnet 50 inside the recess 51, and applying any bonding material or other retaining structure. The contact members 32, 33 may be connected to the carrier 40 by placing the contact members 32, 33 in the positions shown in FIGS. 8-10, with the posts 44 received in the receivers 38 and the electrical contacts 34 received in the slots 49. The subassembly including the carrier 40, as well as the magnet 50 and the contact members 32, 33 connected to the carrier 40, can then be connected to the receptacle 21. This connection can be accomplished by inserting the carrier 40 into the cavity 52 in the receptacle 21. In the embodiment of FIGS. 2-13, the insertion of the carrier 40 causes the retaining tabs 41 to slide into the slots 43 and engage the engagement surfaces 42 to retain the carrier 40 within the cavity 52. When connected in this manner, portions of the contact members 32, 33 are engaged between the carrier 40 and the surfaces of the receptacle 21 that define the cavity 52, and the magnet 50 is engaged between the carrier 40 and the adjacent wall 23 of the receptacle, which adds stability to the connections between the carrier 40 and the magnet 50 and the contact members 32, 33. The bottom of the carrier 40 and the opening 29 of the cavity 52 may then be covered with a covering member 53, as shown in FIG. 13. The covering member 53 may be, e.g., a patch of material or an applied coating that adheres to the components of the housing assembly 19. Additionally, the covering member 53 may be moisture resistant and function to seal the cavity against ingress of moisture, dirt, or other contaminants and/or may be electrically insulative to insulate the contact members 32, 33 against shorting. The housing assembly 19 at this stage can then be connected to the wearable article 10.

Figure 20:
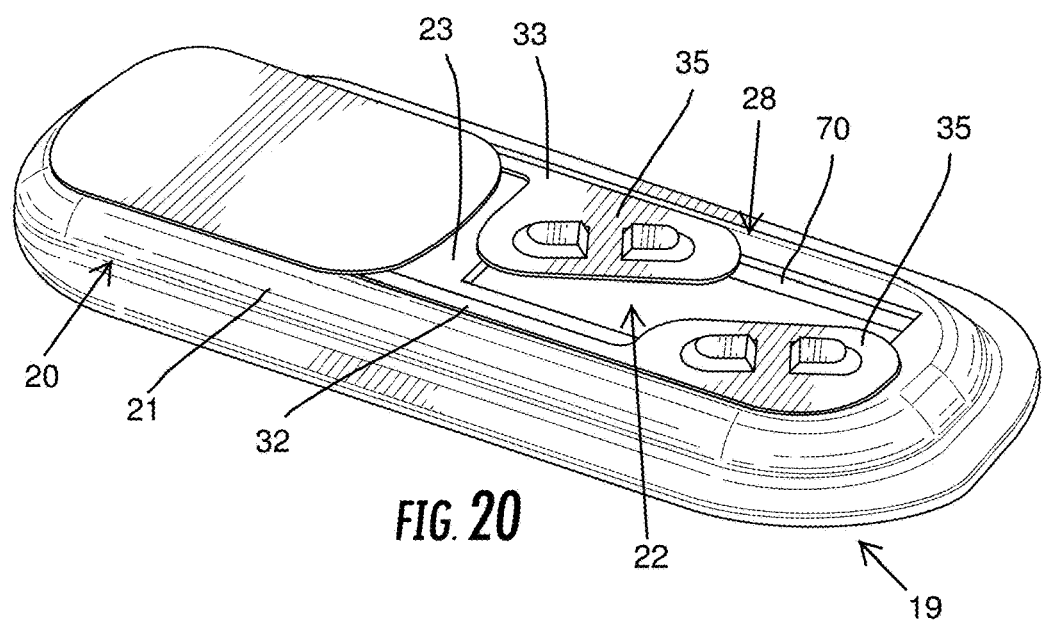
FIG. 20 is a bottom rear perspective view of another embodiment of a housing assembly according to aspects of the present disclosure.
Figure 21:
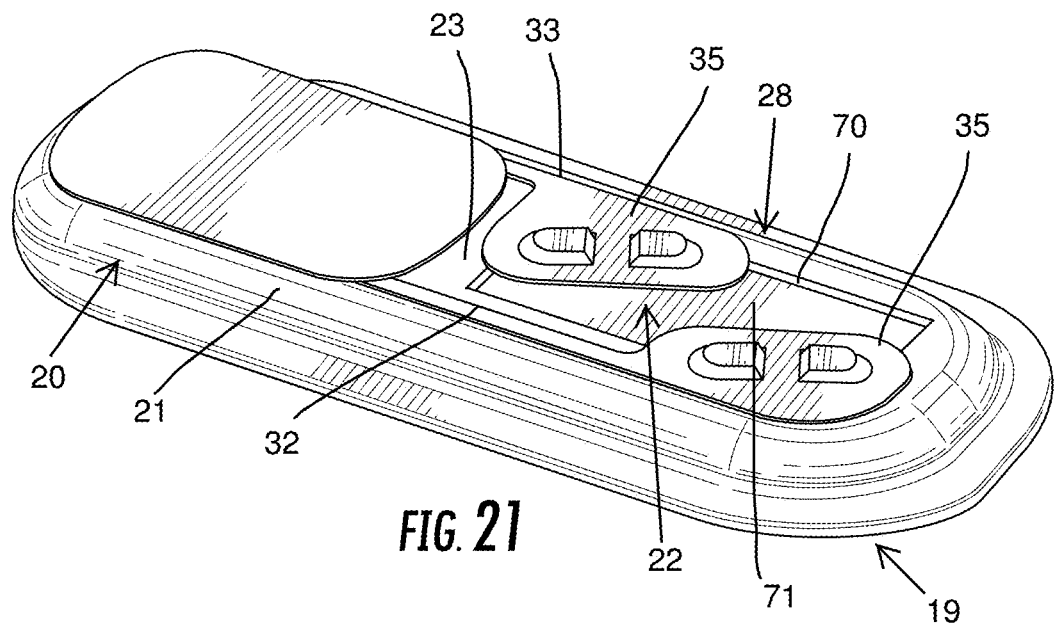
FIG. 21 is a bottom rear perspective view of the housing assembly of FIG. 20.

In one embodiment, the leads 17 are connected to the contact members 32, 33 prior to connection of the housing assembly 19 to the article 10. As discussed above, the leads 17 are connected to contact pads 35 on the contact members 32, 33 in one embodiment, and the leads 17 are connected by winding around projections 37 on the contact pads 35 in the embodiment shown in FIG. 19. In other embodiments, the leads 17 may be connected to the contact members 32, 33 in another configuration, such as the configurations shown in FIGS. 14-15, 22, and 26. Alternately, the leads 17 may be connected to the contact members 32, 33 after the housing assembly 19 is connected to the article 10. In another embodiment, the housing 20 may be provided with access features to access the leads 17 and the contact pads 35 after connection of the housing 20 to the article 10, such as shown in FIGS. 20-21. FIG. 20 illustrates a housing 20 where the receptacle 21 has an opening 70 that extends through the wall 23 forming the bottom side 28 of the receptacle 21, providing access to the leads 17 and the contact pads 35 from within the chamber 22. The opening 70 can be sealed with a cover 71 when the desired access is complete, in order to protect against shock and/or contamination. The cover 71 may be applied on the inner surface of the chamber 22, such as a liquid sealant, a filler resin, or a cover piece connected to the receptacle 21, and the cover 71 may be permanent or removable.

Figure 23:
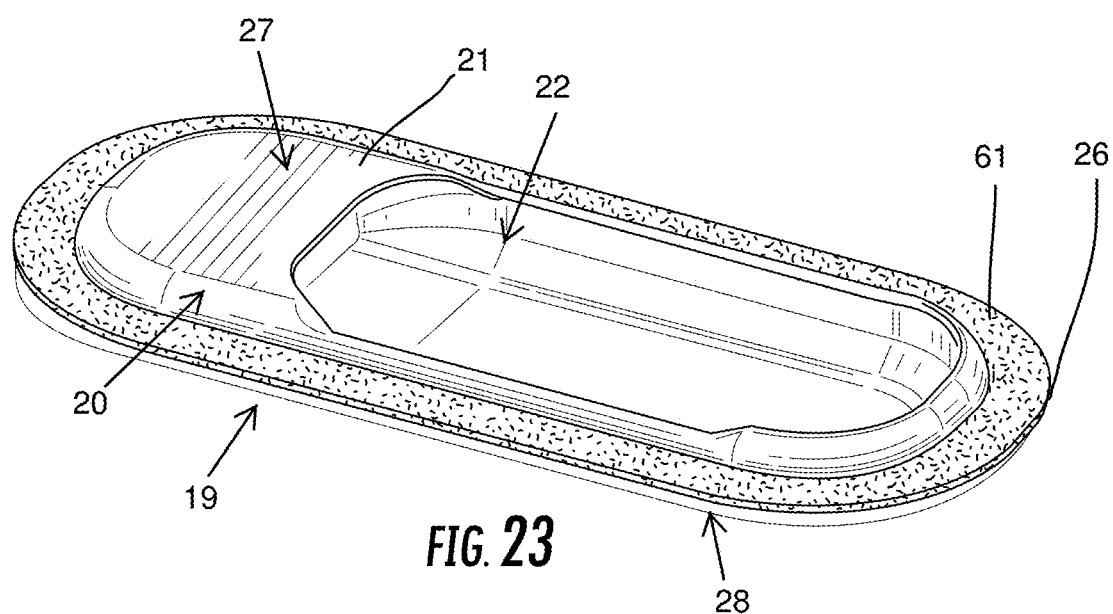
FIG. 23 is a top rear perspective view showing a step in one embodiment of a process for connecting the housing of FIG. 1 to a wearable article, according to aspects of the present disclosure.
Figure 24:
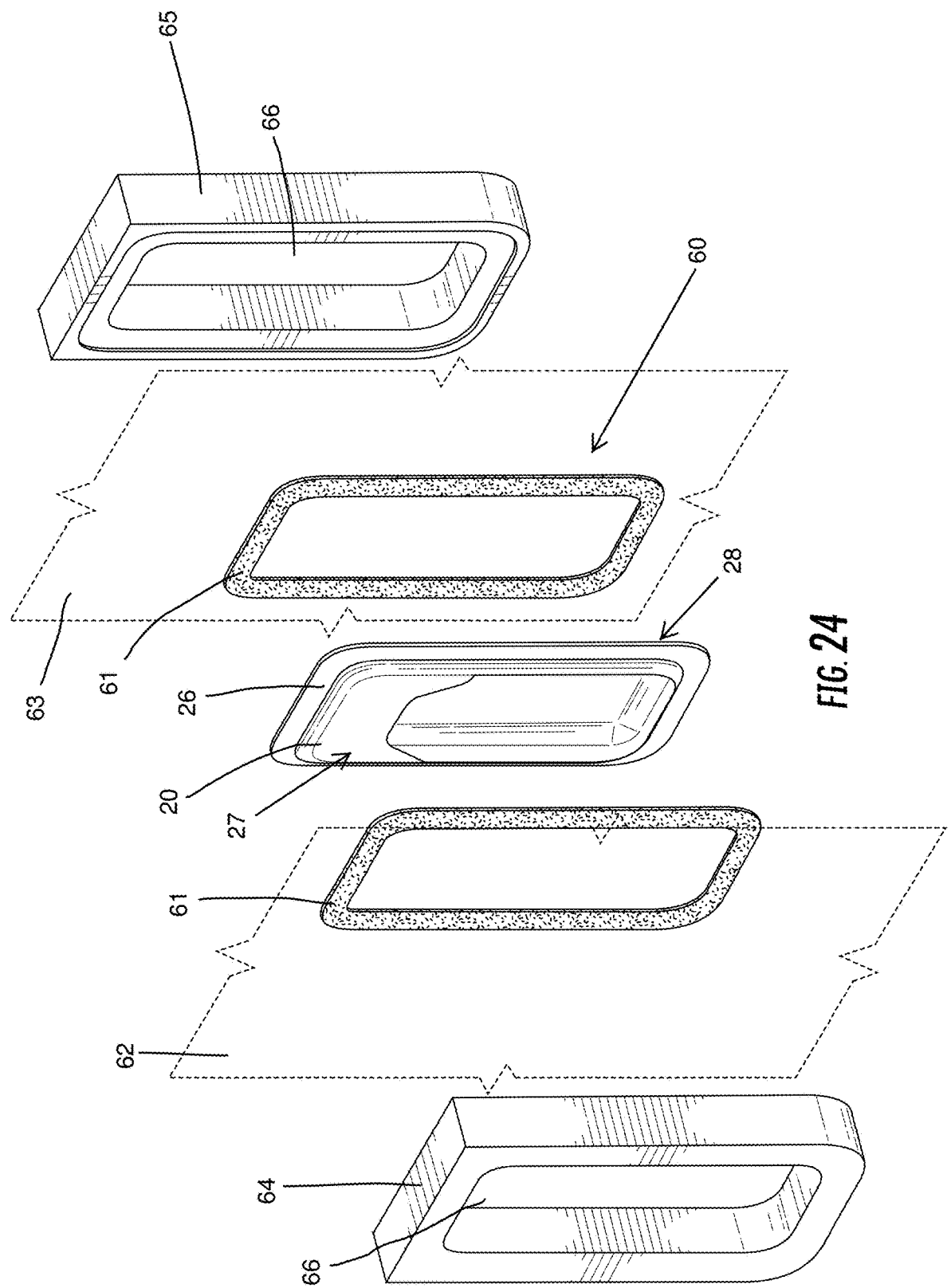
FIG. 24 is an exploded perspective view showing another step in the embodiment of the process for connecting the housing of FIG. 1 to the wearable article.
Figure 25:
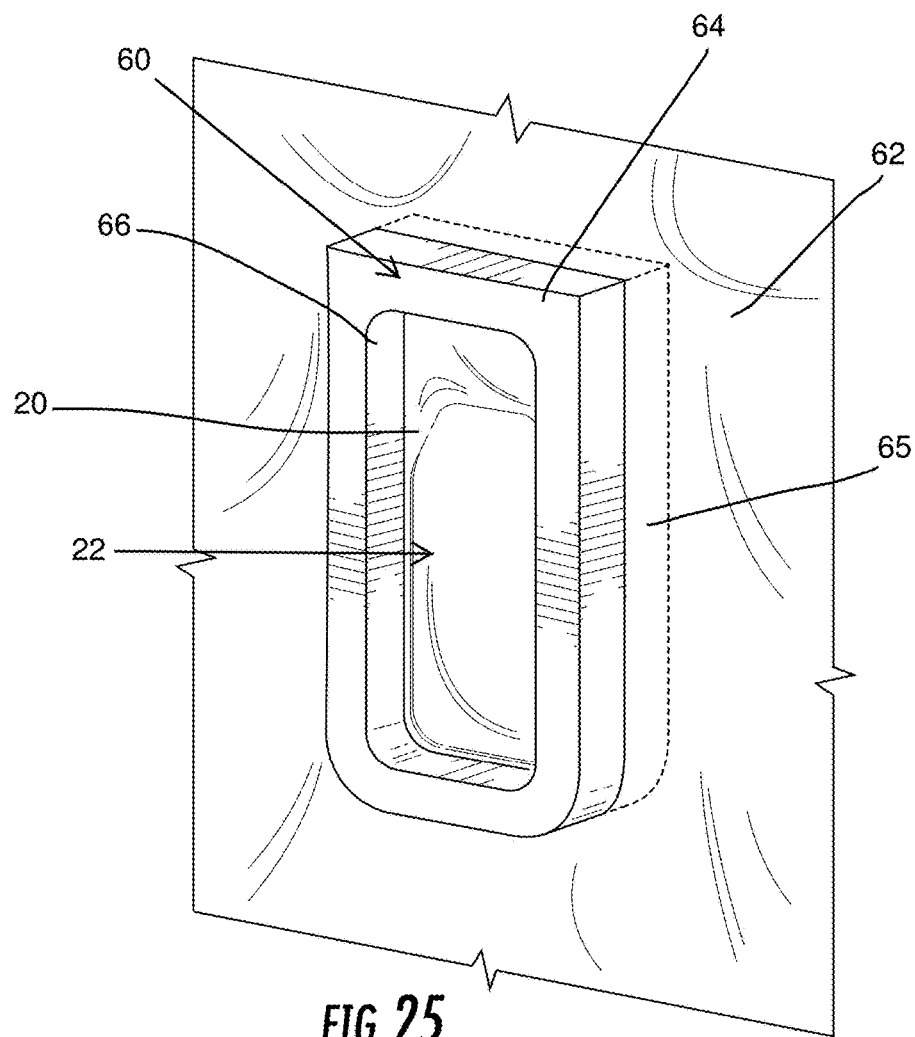
FIG. 25 is a perspective view showing another step in the embodiment of the process for connecting the housing of FIG. 1 to the wearable article.

In one example embodiment, the housing assembly 19 is connected to the article 10 by bonding the housing assembly 19 to the article 10. FIGS. 23-25 illustrate an embodiment of a method and a heat press assembly 60 for bonding a housing assembly 19 to an article 10 using a heat press operation on at least a portion of the housing 20. The heat pressing may utilize a bonding material 61, such as a heat-activated film. The heat press assembly 60 in FIGS. 24-25 is configured for heat pressing around the flange 26 of the housing 20, with the flange 26 being pressed between at least a top layer 62 and a bottom layer 63 of fabric or other material forming the adjacent portions of the article 10. The top and bottom layers 62, 63 may be separate pieces or may be part of a single piece that is folded over to create both layers 62, 63. It is understood that additional layers may be used, and that the top and bottom layers 62, 63 in the embodiment shown in FIGS. 23-25 may include multiple top layers 62 or bottom layers 63, respectively. Prior to heat pressing as shown in FIGS. 23-25, the components to be bonded are assembled in a layered configuration for bonding, such as having the bonding material 61 applied around top and bottom sides of the flange 26 of the housing 20, and the top and bottom layers 62, 63 positioned above the top side and below the bottom side of the flange 26, respectively. In one embodiment, the housing assembly 19 may first be connected to one or both layers 62, 63 of the article 10 by a temporary connection, e.g., by stitching, in order to hold the housing assembly 19 in place during the operation. Heat pressing may be accomplished using any or all of the techniques shown and described in U.S. patent application Ser. Nos. 14/946,682; 14/946,670; 14/946,674; and Ser. No. 14/946,691, or similar techniques.

Figure 27:
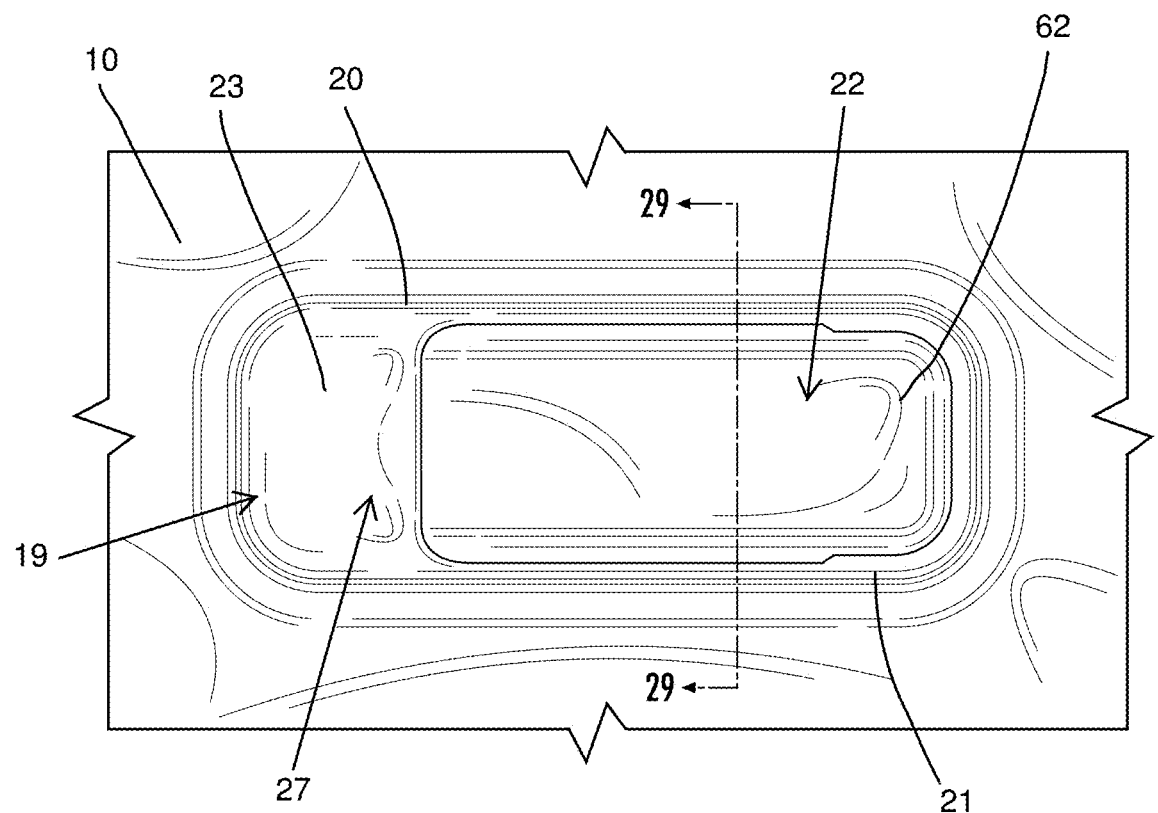
FIG. 27 is a plan view of another embodiment of a housing assembly connected to a wearable article according to aspects of the disclosure.
Figure 28:
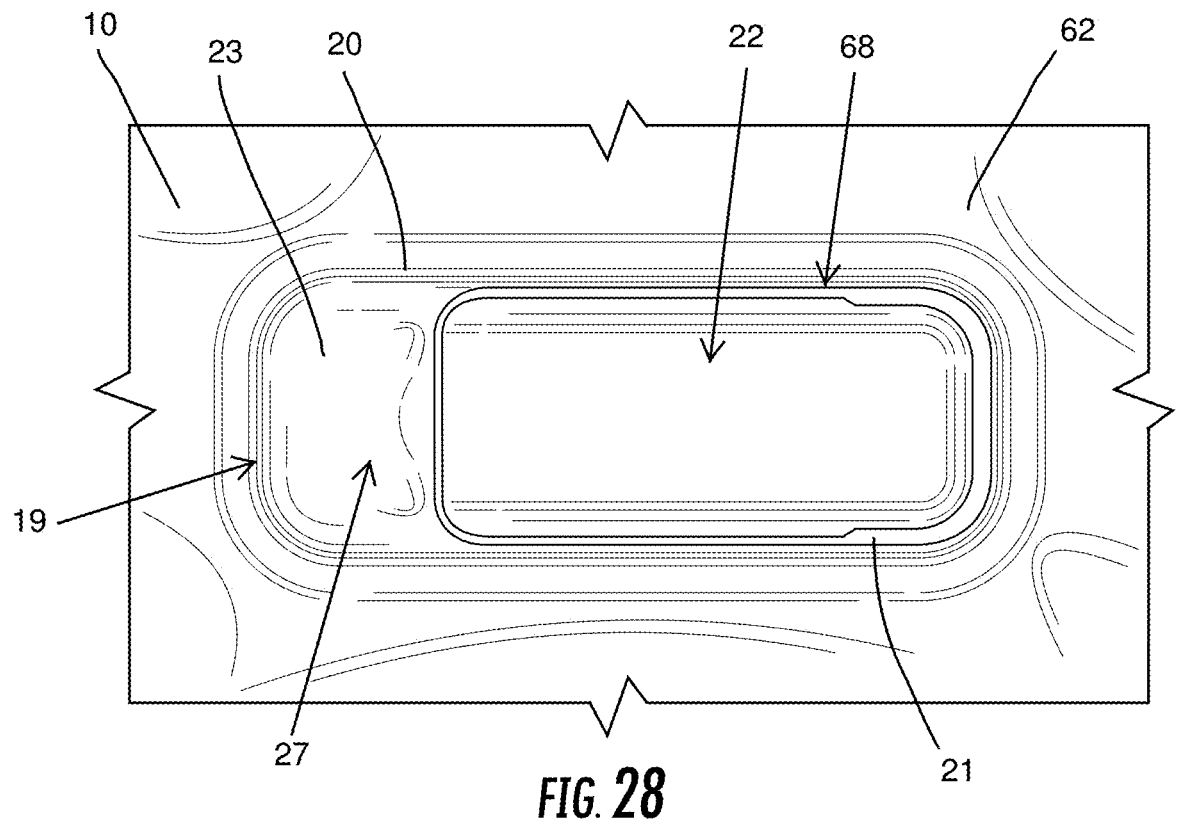
FIG. 28 is a plan view of another embodiment of a housing assembly connected to a wearable article according to aspects of the disclosure.
Figure 29:
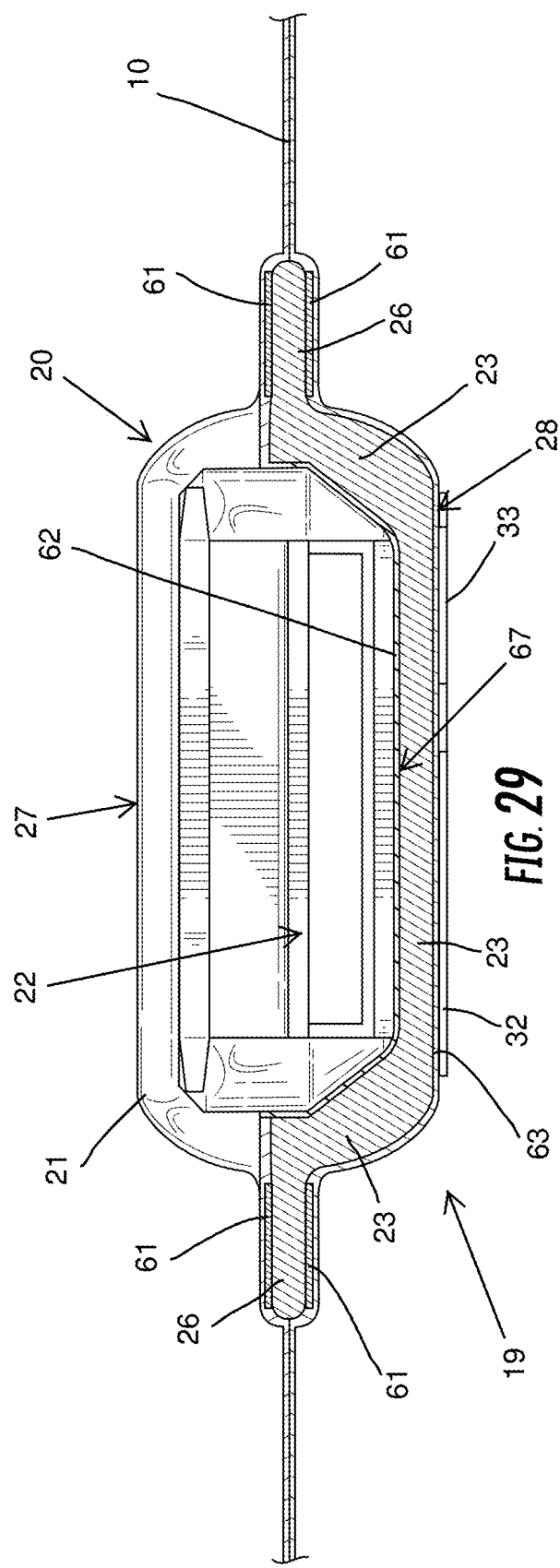
FIG. 29 is a cross-section view taken along lines 29-29 of FIG. 27.

The heat press assembly 60 as shown in FIGS. 24-25 includes two opposed mold pieces 64, 65 that are annular in shape, each having an internal opening 66, so that the mold pieces 64, 65 are configured to press only around the flange 26 of the housing 20. In this configuration, the main body of the housing 20 is received within the opening 66, so that the mold pieces 64, 65 do not press the main body of the housing 20 or the adjacent portions of the layers 62, 63, which localizes the heat application and avoids creating unwanted marks or discolorations on the non-pressed portions of the article 10 and the housing 20. In the embodiment shown in FIGS. 23-25, the layers 62, 63 of the material cover both the top and bottom sides 27, 28 of the receptacle 21. In this configuration, a hole or slit (not shown) is formed in the top layer 62 to provide access to the interface 31, and another hole or slit (not shown) is formed in the bottom layer 63 to provide access to the contact pads 35. The top layer 62 may be pushed down into the chamber 22 of the receptacle 21, as shown in FIGS. 27 and 29, and the arms 36 and contact pads 35 of the contact members 32, 33 may extend through the bottom layer 63 and be located below the bottom layer 63, as shown in FIGS. 19 and 29. In one embodiment, the top layer 62 may further be bonded to the housing 20 within the chamber 22 of the receptacle 21, such as by application of additional bonding material between the top layer 62 and one or more interior surfaces of the receptacle 21, such as at a location 67 as shown in FIG. 29. The additional bonding material may be heat pressed, either by modification of the top die 64 to heat press in the desired location or by use of a separate die (not shown) in the same or a subsequent heat pressing operation. Alternately, the additional bonding material may not require heat pressing, such as glue, cement, or other adhesive. Other portions of the housing 20 may be bonded to the layers 62, 63 in a similar manner In another embodiment, a larger opening may be cut in the top layer 62, such as an opening 68 approximately the same size as the access opening 24 of the receptacle 21, as shown in FIG. 28.

After the leads 17 are connected to the contact members 32, 33 and the housing assembly 19 is connected to the article 10, an insulative material 69 may be applied to cover part or all of the exposed portions of the electrical connecting structure 30 in one embodiment, as shown in FIG. 19. In this embodiment, the insulative material 69 covers at least the contact pads 35 and the connections to the leads 17. The insulative material 69 in the embodiment of FIG. 19 covers all portions of the electrical connecting structure 30 that are exposed on the exterior of the housing 20 and below the bottom side 28 of the receptacle 21, including the contact pads 35 and portions of the arms 36 of the contact members 32, 33 that are not already covered by the covering member 53, as well as portions of the leads 17. This insulative material 69 resists shorts and shocks that may occur if both of the contact members 32, 33 are contacted when electrical power is applied. The insulative material 69 may also provide at least some sealing of the electrical connecting structure 30 against ingress of environmental materials, especially moisture. This is particularly advantageous when the housing assembly 19 is connected to an athletic garment, as perspiration could affect the functioning of the module 80 and/or the electrical connecting structure 30, as well as increase the risk of shocks. The insulative material 69 may be the same material used for the covering member 53 in one embodiment. Examples of materials that may be used as the insulative material 69 and/or the material of the covering member 53 include a patch of material or an applied coating that adheres to the components of the housing assembly 19.

In other embodiments, different connection techniques may be used to connect the housing assembly 19 to an article 10 that do not utilize heat pressing, such as by using a different bonding material 61 or by using mechanical connection techniques such as sewing or fasteners. Additionally, the housing assembly 19 can be used in connection with non-wearable articles 10 in other embodiments. The housing assembly 19 provides numerous advantages that can be realized when connected to a wearable article 10 using any connection technique, and that can also be realized when used in connection with a different type of article 10.

Figure 30:
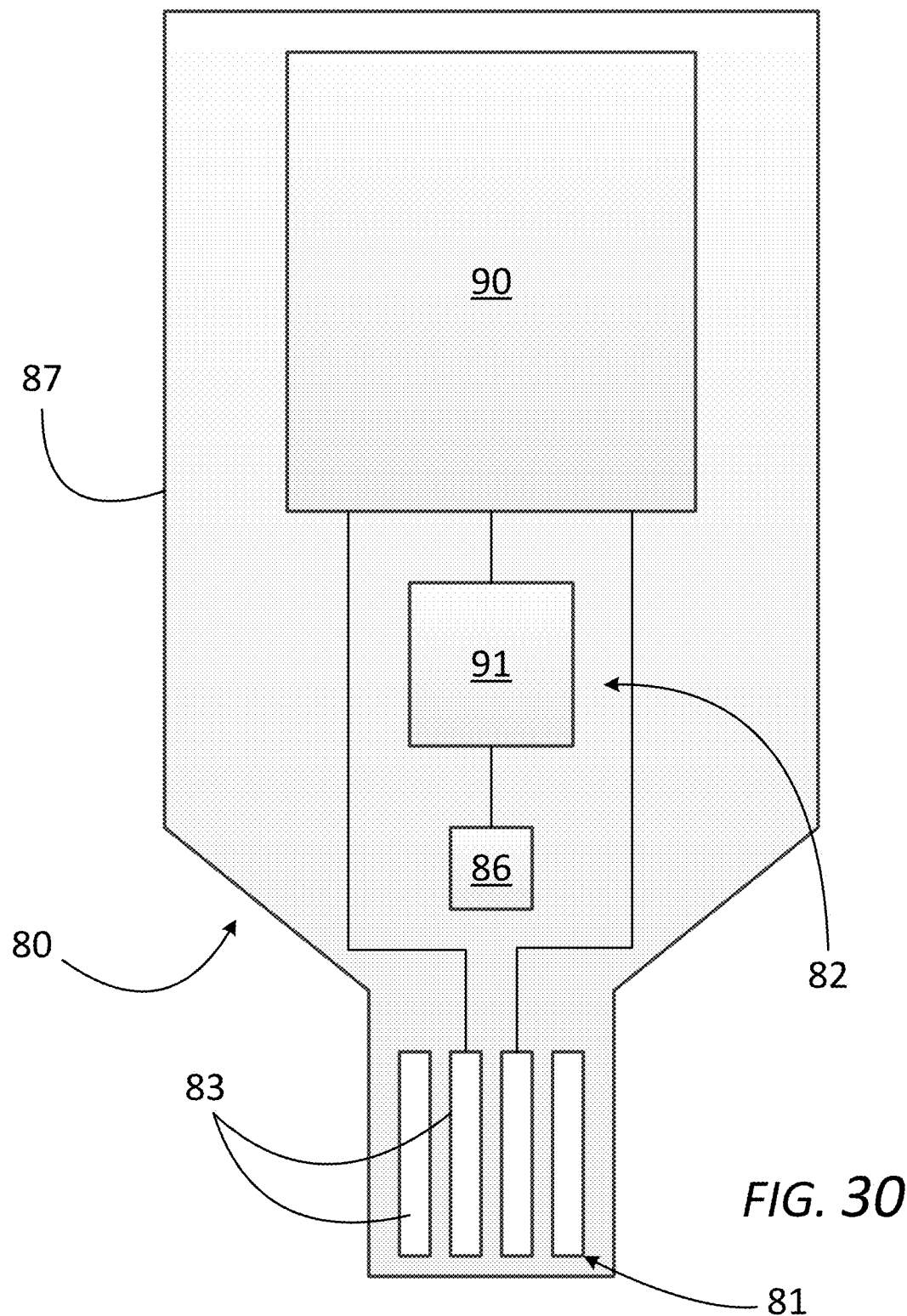
FIG. 30 is a schematic view of one embodiment of an electronic module according to aspects of the disclosure.
Figure 31:
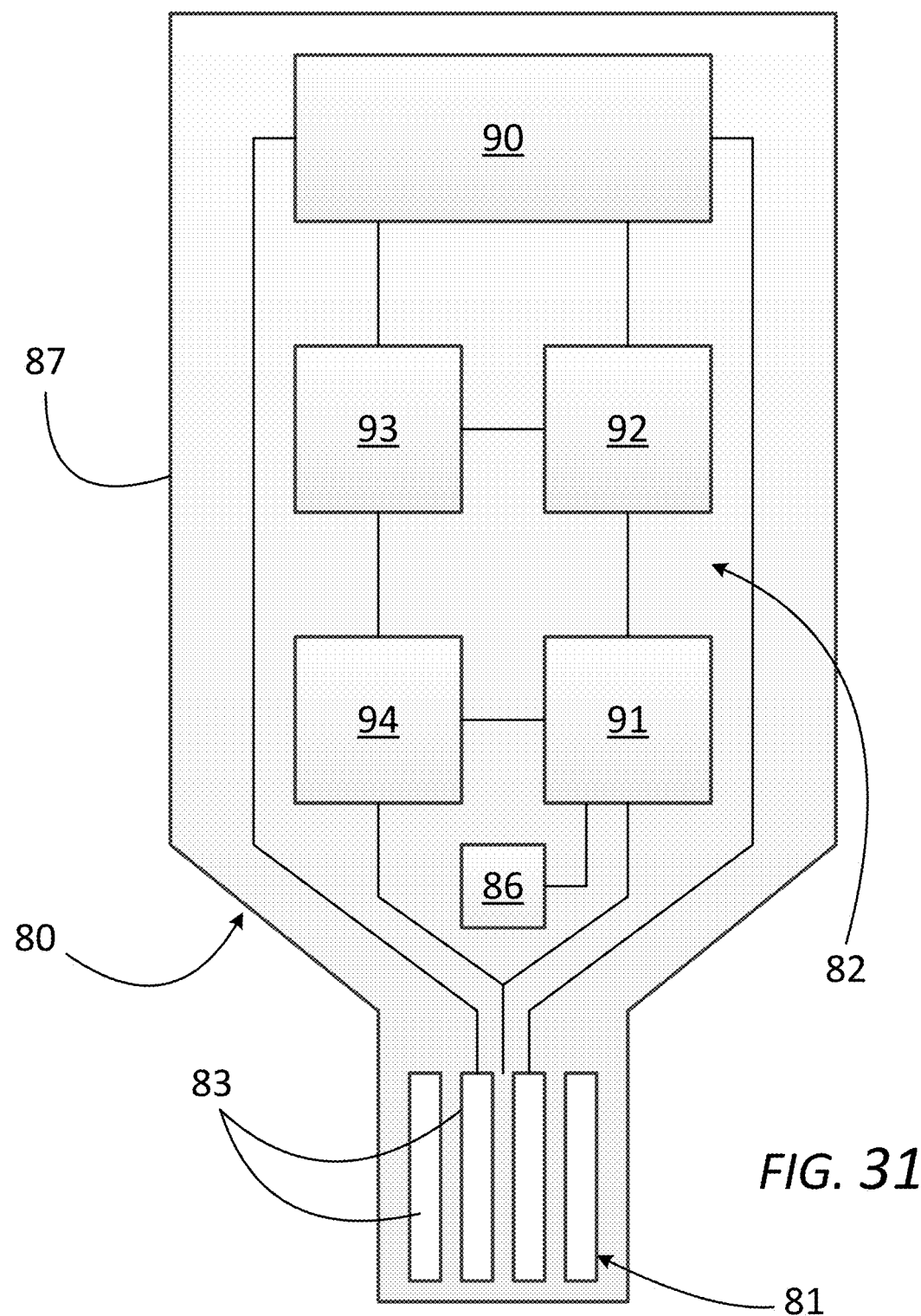
FIG. 31 is a schematic view of another embodiment of an electronic module according to aspects of the disclosure.

An example of an electronic module 80 that is usable in connection with the system 12 and/or the housing assembly 19 is shown in FIGS. 1-3 and 11. As illustrated in FIGS. 1-3 and 11, the module 80 in this embodiment includes a casing 87 that supports an external connector 81 and contains one or more electronic components 82. The external connector 81 may have various configurations depending on the intended usage of the module 80. In the embodiment of FIGS. 1-3 and 11, the connector 81 is a USB-format connector that includes a plurality of terminals 83, which can be connected to a USB port, such as for charging and/or communication with a computer device connected to the port. FIGS. 30 and 31 illustrate embodiments of the module 80 schematically. The electronic components 82 may include at least a power source 90 in one embodiment, and may include additional electronic components, including a processor 91, a memory 92, an input-output device (I/O) 93, a transmitter/receiver (TX/RX) 94, and/or other components as illustrated in FIGS. 30 and 31 and described in greater detail herein. FIG. 30 illustrates one embodiment, where the module 80 is configured for use in supplying power only, and not for data collection, performance monitoring, or communication. In this embodiment, the module 80 includes a power source 90, a processor 91 (which may be in the form of a printed circuit board), and a magnetic sensor 86 as described in greater detail below. Other components, such as a memory, may be included in other embodiments. FIG. 31 illustrates another embodiment, where the module 80 is configured for multiple functions, including supplying power as well as data collection, performance monitoring, and/or communication. In this embodiment, the module 80 additionally includes a memory 92, an I/O 93, and a TX/RX 94. The module 80 may include additional components, such as sensors as described herein which are not illustrated for the sake of simplicity, and it is understood that the module 80 may include further additional or alternate components in other embodiments.

The connector 81 may be connected to one or more electronic components 82 of the module 80. For example, in the embodiment of FIGS. 1-3 and 11, the module 80 is configured for providing electric power output through the connector 81, and the connector 81 is connected to the power source 90 in order to do so, as shown in FIGS. 30 and 31. Additionally, in the embodiment of FIGS. 1-3 and 11, the connector 81 has a plurality of terminals 83 (four in the embodiment shown), and only two of the terminals 83 are actively engaged by the interface 31, such that additional terminals 83 are not engaged. More specifically, in the embodiment of FIGS. 2-13, the interface 31 includes two 34 electrical contacts (power and ground), and when the module 80 of FIGS. 1-3 and 11 is inserted into the housing 20, the power contact 34 engages a first terminal 83 and the ground contact 34 engages a second terminal 83 of the plurality of terminals 83 of the connector 81. In this configuration, the power supply 90 of the module 80 is configured to supply power through the power and ground contacts 34 via the two active terminals 83, and the remainder of the terminals 83 of the connector 81 are inactive or not actively engaged by the interface 31, as illustrated in FIG. 30. This configuration enables the connector 81 to be configured as a USB-format connector that is configured for insertion into a USB port of a computer device, while also functioning to supply power through an interface 31 with only two electrical contacts 34.

In another embodiment, the module 80 may additionally or alternately be configured for transmitting and receiving data, instructions, and other information through the connector 81. The connector 81 in this embodiment may be connected to the processor 91, the memory 92, the TX/RX 94, and/or other components in order to enable this functionality, as shown in FIG. 31. For example, the module 80 and the connector 81 may be configured for receiving data through the interface 31 from other components in communication with the interface, such as a movement sensor (e.g., accelerometer, gyroscope, force sensor, angular rate sensor, compass, etc.), a location-determining device (e.g., GPS), a light (including non-visible light) sensor, a temperature sensor (including ambient temperature and/or body temperature), a sleep pattern sensor, a heart rate monitor, an image-capturing sensor, and/or a moisture sensor, among others. As another example, the module 80 and the connector 81 may also be configured for transmitting instructions through the interface 31 to control other components in communication with the interface 31. As a further example, the module 80 and the connector 81 may be configured for communication through a port on a separate computer device, such as by removal of the module 80 from the housing 20 and insertion of the connector 81 into the port, as described above. It is understood that such communication with other components may be accomplished wirelessly or by use of multiple connectors 81 in other embodiments.

The module 80 may further include one or more buttons 84 that are configured to control operation of the electronic component(s) 82. For example, in the embodiment of FIGS. 1-3, the module 80 includes a single button 84 configured for use as a "power" button, to activate or deactivate the output of the power supply 90 through the connector 81. The casing 87 and the connector 81 of the module 80, and the button 84 if present, may also be sealed against ingress of moisture, which can be particularly advantageous when used in connection with articles 10 for athletic use. In one embodiment, the sealing can be accomplished by ultrasonic welding around any junctures 85 in the casing 87 and around any junctures between the casing 87 and the terminals 83 or the button 84.

Figure 2:
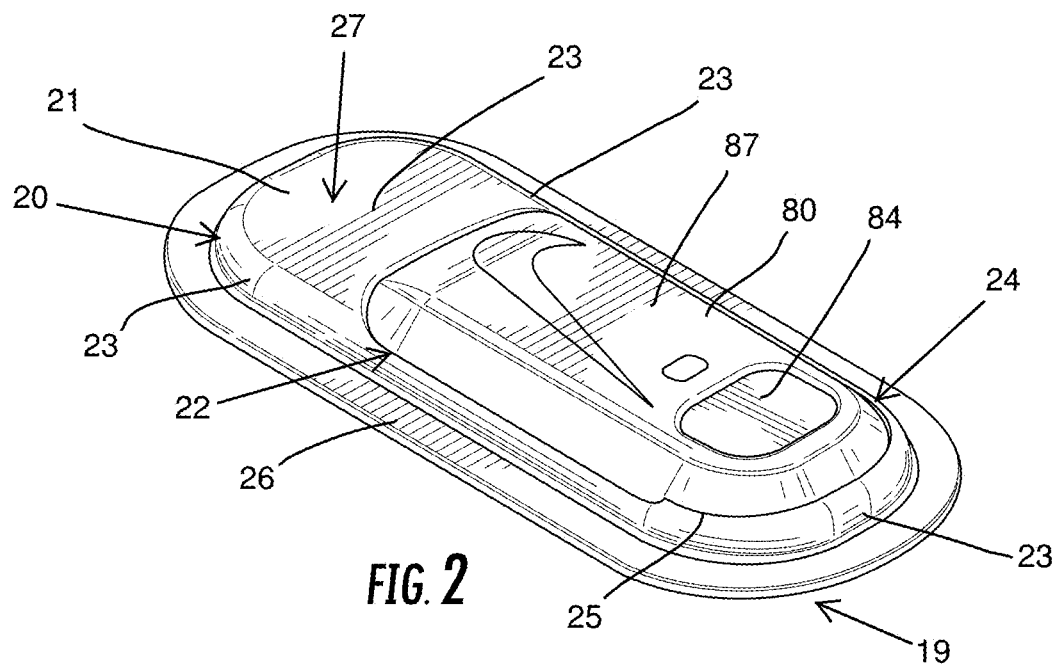
FIG. 2 is a top rear perspective view of the module of FIG. 1 engaged with one embodiment of a housing according to aspects of the present disclosure.
Figure 3:
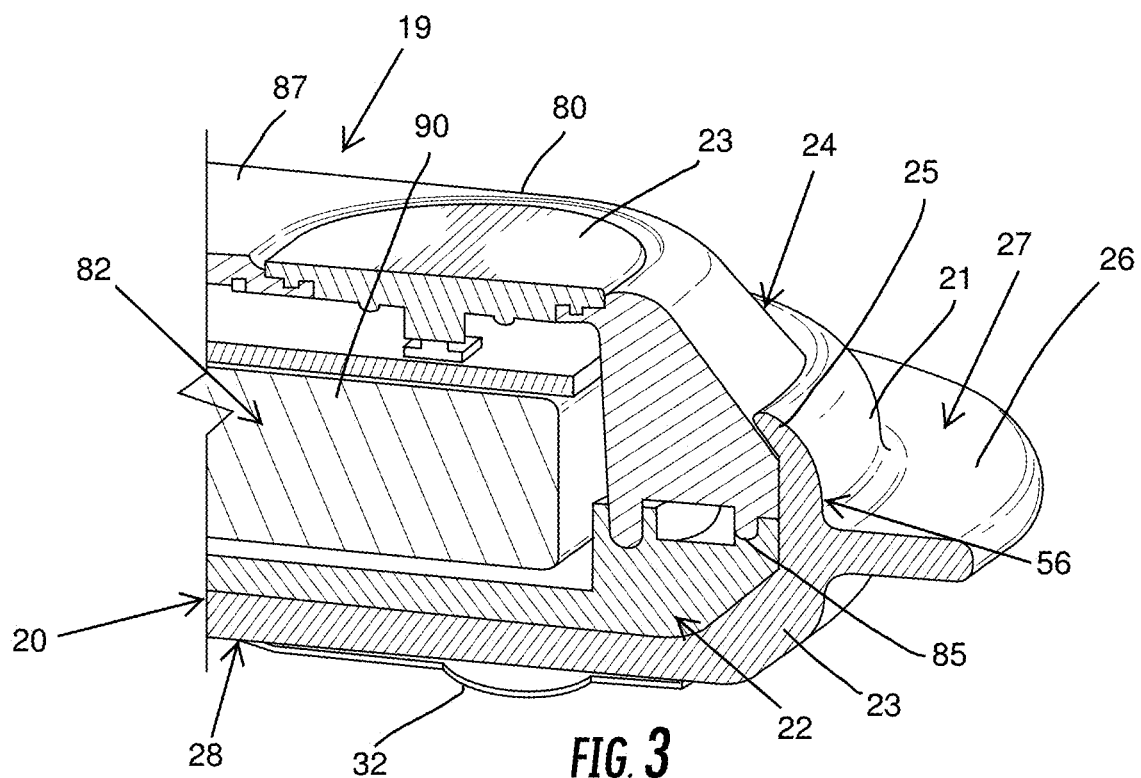
FIG. 3 is a partial cross-sectional view of the housing and the module of FIG. 2.
Figure 4:
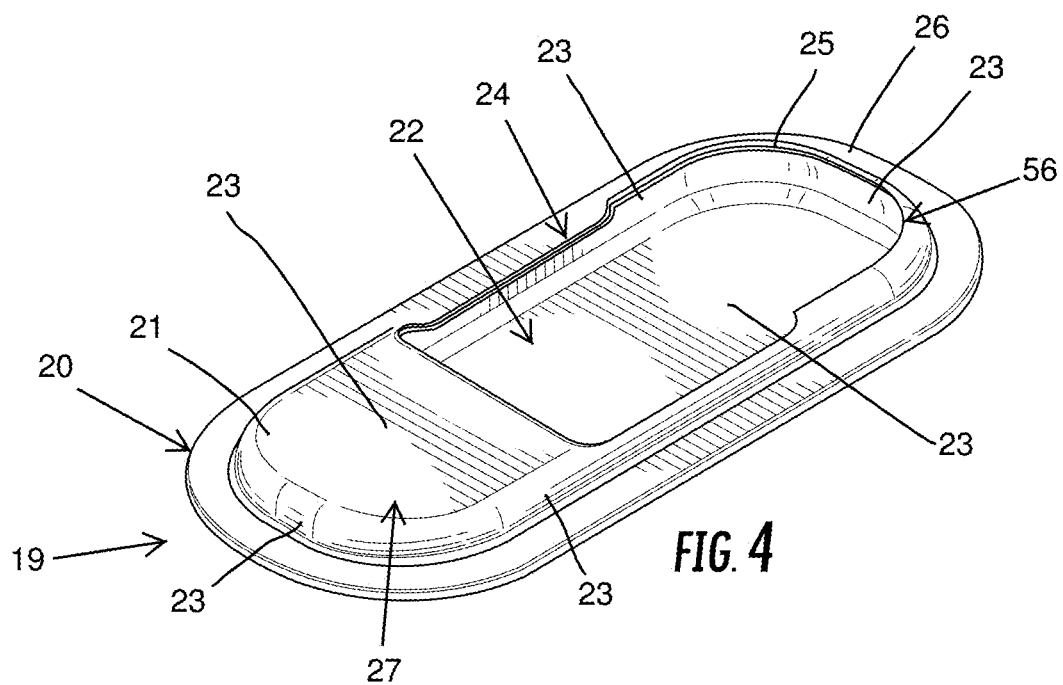
FIG. 4 is a top front perspective view of the housing of FIG. 2.
Figure 5:
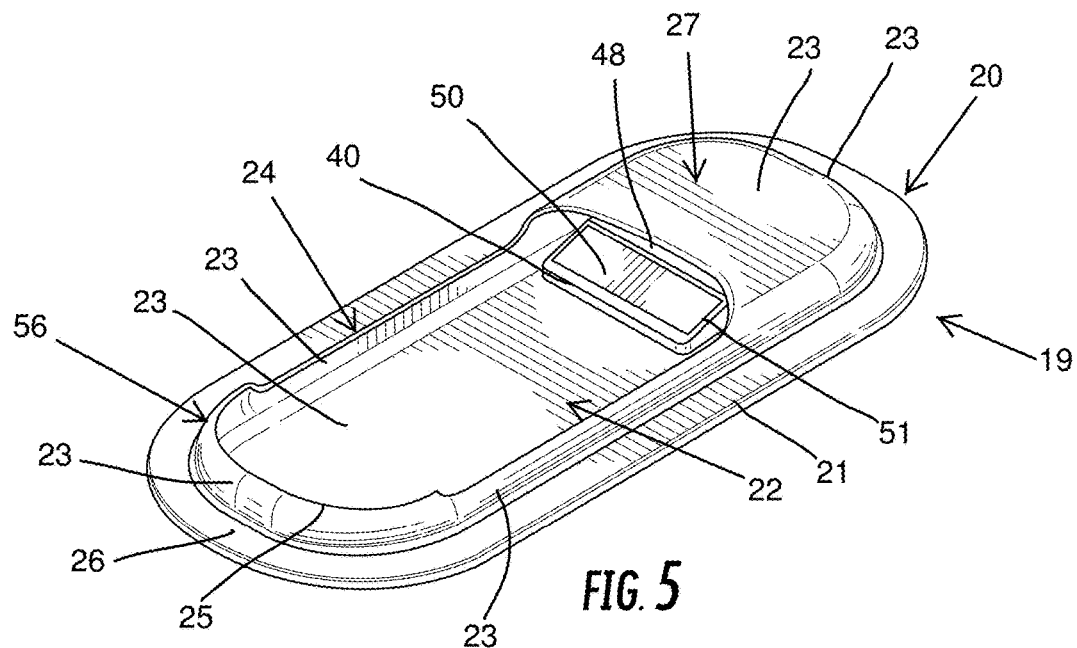
FIG. 5 is a top rear perspective view of the housing of FIG. 2.

The housing 20 includes structures to physically and electronically engage the module 80 when the module 80 is received in the housing 20. The interface 31 and the electrical contacts 34 thereof, which function to physically and electronically engage the connector 81 of the module 80 as described above. The carrier 40 engages the top, bottom, and sides of the end of the connector 81, as shown in FIG. 11. In this configuration, the shelf 46 and the base 48 engage the top and bottom of the connector 81, and the shelf 46, the column 47, and the base 48 combine to define a receiver 57 configured to receive the end of the connector 81. The carrier 40 also has sidewalls 58 that extend between the shelf 46 and the base 48 to further define sides of the receiver 57. The walls 23 of the receptacle 21 also define portions of the receiver 57 in this embodiment, including the walls 23 on the top and bottom sides 27, 28 of the receptacle 21 and the adjacent walls 23 on the sides of the receptacle 21. The base 48 of the carrier 40 and the wall 23 on the bottom side 28 of the receptacle 21 combine to create a ramped surface 59 leading into the receiver 57, and the wall 23 on the top side 27 of the receptacle 21 similarly defines a ramped surface 59, to ease insertion of the connector 81. The receiver 57 and the structures defining the receiver 57 also enclose the connector 81 in order to protect it from inadvertent shorting, dirt, dust, moisture, etc. The lip 25 around at least a portion of the access opening 24, further engages the module 80 to retain the module 80 within the chamber 22, as illustrated in FIGS. 2-3. In this embodiment, the lip 25 extends inwardly around only a portion of the access opening 24, including across the end 56 of the opening 24 opposite the interface 31 and down a portion of each side 24 of the opening 24 adjacent the end 56. Configured in this way, the structures of the carrier 40 and the receptacle 21 around the receiver 57 retain the connector 81 of the module 80 and the lip 25 retains the end of the module 80 opposite the connector 81, thus creating a stable, multi-point retaining structure. In other embodiments, the module 80 may be engaged and retained by the housing 20 in other ways, using different connecting and retaining structure.

The module 80 may be configured with a lockout feature that functions to prevent activation of the terminals 83 of the connector 81 when the module 80 is not engaged with the housing 20 and/or the interface 31. In the embodiment of FIGS. 1-13, the module 80 includes a magnetic sensor 86, such as a Hall effect sensor, that is configured to detect the magnet 50 when in proximity to the magnet 50. The magnetic sensor 86 is shown schematically in FIG. 11, and the magnetic field of the magnet 50 is sufficient such that the magnetic field extends into the chamber 22 and is detectable by the sensor 86 when the module 80 is received in the chamber 22. The module 80 in this embodiment is configured to deactivate the connector 81 when the sensor 86 does not sense the magnet 50 and to activate the connector 81 when the sensor 86 does sense the magnet 50. The module 80 only supplies power from the power source 90 through the terminals 83 when the connector is activated, i.e., when the module 80 is engaged with the housing 20 and the interface 31 thereof. This lockout feature increases safety of the module 80, because a short or shock could occur if a user contacts both of the terminals 83 when the module 80 is active outside the receptacle 21.

Figure 32:
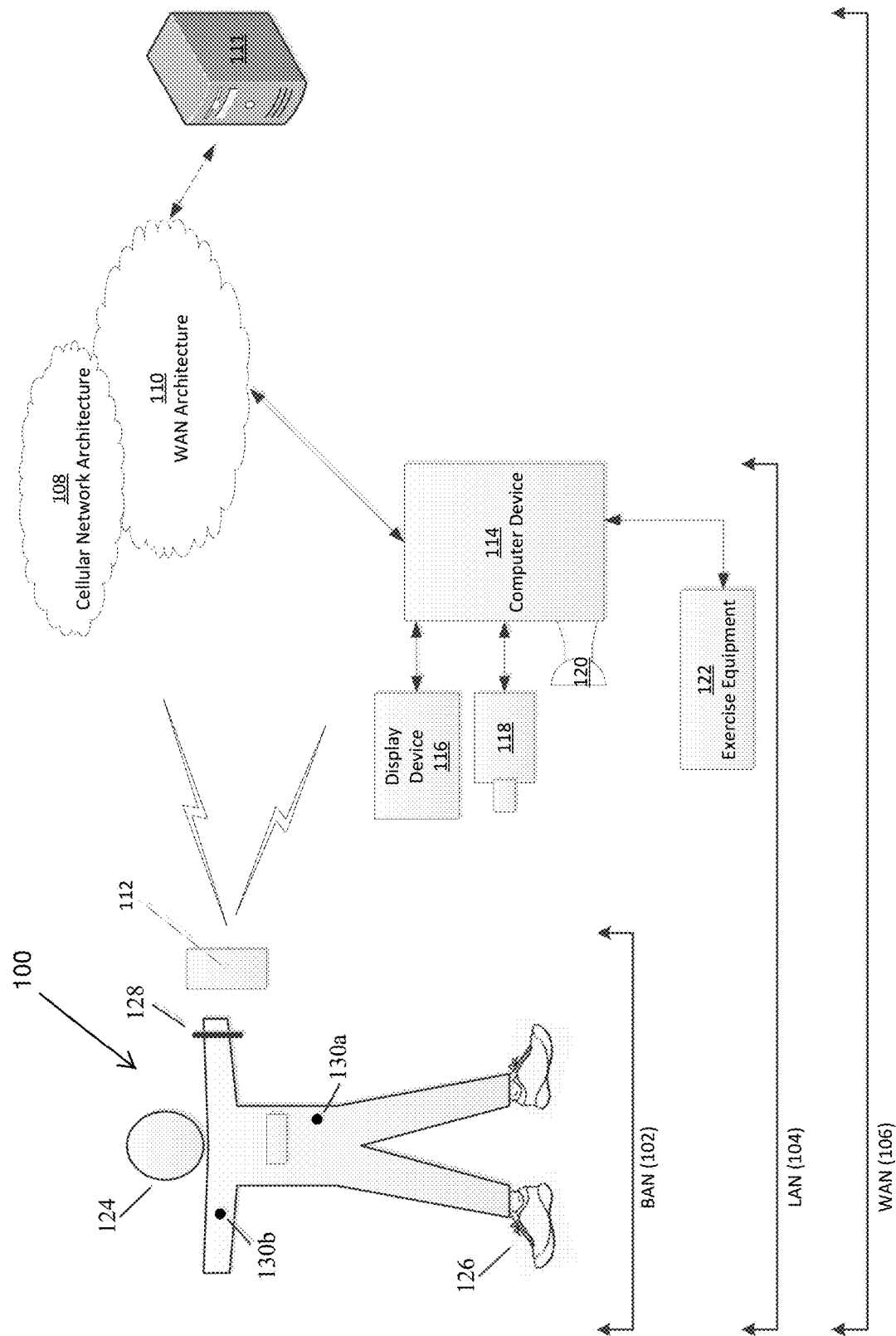
FIG. 32 illustrates an example system that may be configured to provide personal training and/or obtain data from the physical movements of a user in accordance with example embodiments.
Figure 33:
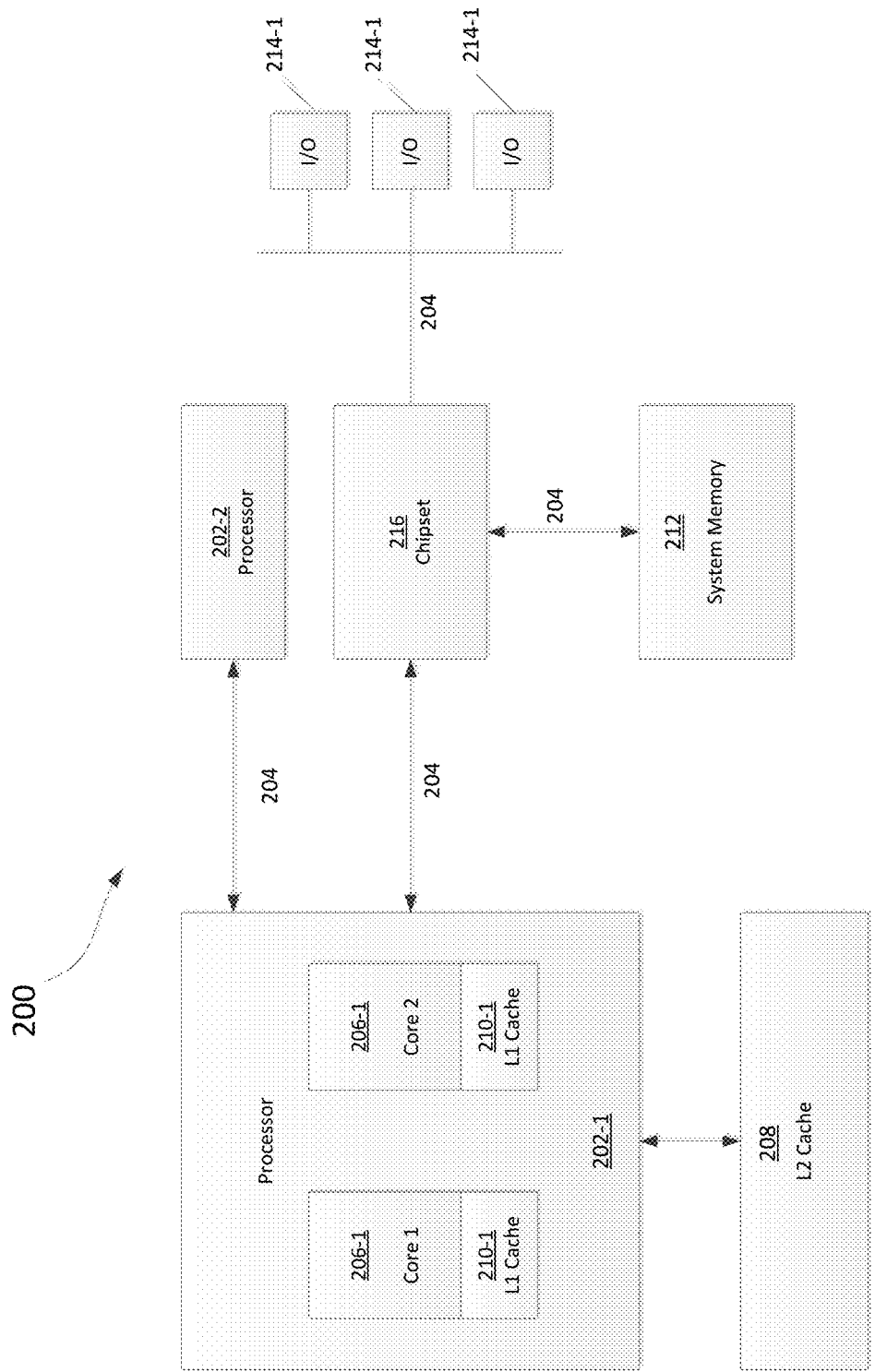
FIG. 33 illustrates an example computer device that may be part of or in communication with the system of FIG. 32.

Aspects of this disclosure relate to systems and methods that may be utilized across a plurality of networks. In this regard, certain embodiments may be configured to adapt to dynamic network environments. Further embodiments may be operable in differing discrete network environments. For example, the module 80 described herein may include components and functionality to enable such utilization in some embodiments. FIGS. 32 and 33 illustrate structural and functional embodiments of computer devices, as well as operation of the computer devices within various network environments. The module 80 and/or any computer devices communicating with the module 80 may be embodied by the embodiments shown in FIGS. 32 and 33. FIG. 32 illustrates an example of a system 100 in accordance with example embodiments, which may be embodied as a personal training system. Example system 100 may include one or more interconnected networks, such as the illustrative body area network (BAN) 102, local area network (LAN) 104, and wide area network (WAN) 106. As shown in FIG. 32 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 32, (such as portable electronic device 112 or any other device described herein) may be considered inclusive to one or more of the different logical networks 102-106. With the foregoing in mind, example components of an illustrative BAN and LAN (which may be coupled to WAN 106) will be described.

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Those skilled in the art will appreciate that the design and structure of computer device 114 may vary depending on several factors, such as its intended purpose. One example implementation of computer device 114 is provided in FIG. 33, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 32, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 33. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise equipment 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided herein.

User 124 may be associated with (e.g., possess, carry, wear, and/or interact with) any number of devices, such as portable device 112, one or more body-mounted devices such as a shoe-mounted device 126 or an arm-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 32-33 and other locations herein, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114.

It is understood that any of the embodiments of housings, modules, wearable articles, systems, and other components and methods described herein may include any of the features described herein with respect to other embodiments described herein, including structural features, functional features, process steps, and/or properties, unless otherwise noted. It is understood that the specific sizes, shapes, orientations, and locations of various components of the housings, modules, wearable articles, and systems described herein are simply examples, and that any of these features or properties may be altered in other embodiments.

The various embodiments of housings, modules, wearable articles, systems described herein can provide advantages over existing technology. For example, the housing assembly and connecting structure described herein provides a secure way of mounting a removable electronic module on a wearable article that permits the connection of power leads to the module. This, in turn, permits the wearable article to include an electrically-powered component. These structures also provide a configuration for mounting such a removable module while retaining comfort and full range of motion for the user. The insulative materials and lockout feature of the housing assembly provide the further advantage of avoiding the risk of shocking the user by contact with the power leads. The manufacturing methods described herein provide efficient and effective techniques for connecting the housing assembly to a wearable article, particularly an article of apparel or other article made from a fabric material. Other benefits can be recognized and appreciated by those skilled in the art.

While the invention has been described with respect to specific examples including presently preferred modes of carrying out the invention, those skilled in the art will appreciate that there are numerous variations and permutations of the above described systems and methods. Thus, the spirit and scope of the invention should be construed broadly as set forth in the appended claims.

What is claimed is:

1. A housing comprising:
   a receptacle having a plurality of walls defining a chamber and having an opening through at least one of the walls providing access to the chamber, such that the receptacle is configured to removably receive an electronic module within the chamber by insertion of the electronic module through the opening;
   an interface comprising a plurality of electrical contacts exposed within the chamber and configured for removable electronic connection to a connector of the electronic module when the electronic module is received in the chamber;
   a carrier connected to the receptacle and configured to support the contacts of the interface to be exposed within the chamber; and
   a magnet connected to the housing and configured such that a magnetic field of the magnet penetrates the chamber, wherein the magnet is mounted between the carrier and one of the walls of the receptacle, such that the carrier and the receptacle engage the magnet to retain the magnet in place,
   wherein the carrier includes a recess and the magnet is mounted within the recess adjacent to the chamber.

2. The housing of claim 1, wherein the magnet is embedded within the housing and is not physically exposed to the chamber.

3. The housing of claim 1, wherein the receptacle has a plurality of walls defining the chamber, and wherein the magnet is mounted on an outer surface of one of the plurality of walls.

4. A system comprising the housing of claim 1 and the electronic module, wherein the electronic module comprises a sensor configured to sense the magnet when the electronic module is received in the chamber, and wherein the electronic module is configured to deactivate the connector when the sensor does not sense the magnet, and the electronic module is configured to activate the connector when the sensor does sense the magnet.

* * * * *

UNITED STATES PATENT AND TRADEMARK OFFICE
CERTIFICATE OF CORRECTION

| | |
|---|---|
| PATENT NO. | : 11,666,105 B2 |
| APPLICATION NO. | : 15/951743 |
| DATED | : June 6, 2023 |
| INVENTOR(S) | : Donohoe et al. |

It is certified that error appears in the above-identified patent and that said Letters Patent is hereby corrected as shown below:

On the Title Page

Page 4, Column 1, Other Publications, Line 11:
Delete "Internatinal" and insert -- International -- therefor Page 4, Column 1, Other Publications, Line 13:
Delete "Retreived" and insert -- Retrieved -- therefor Page 4, Column 2, Other Publications, Line 7:
Delete "Rerieved" and insert -- Retrieved -- therefor Signed and Sealed this
Twenty-eighth Day of November, 2023

Katherine Kelly Vidal
*Director of the United States Patent and Trademark Office*